US012558530B2

(12) United States Patent
Corey et al.

(10) Patent No.: US 12,558,530 B2
(45) Date of Patent: Feb. 24, 2026

(54) SENSING EVOKED COMPOUND ACTION POTENTIAL (ECAP)

(71) Applicant: Medtronic, Inc., Minneapolis, MN (US)

(72) Inventors: Robert A. Corey, Arden Hills, MN (US); Joel A. Anderson, Brooklyn Park, MN (US); David A. Dinsmoor, North Oaks, MN (US); Kristin N. Hageman, Dayton, MN (US); Scott R. Stanslaski, Shoreview, MN (US); Todd V. Smith, Shoreview, MN (US); Heba Tareq Omar, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 372 days.

(21) Appl. No.: 18/161,499

(22) Filed: Jan. 30, 2023

(65) Prior Publication Data

US 2023/0264014 A1     Aug. 24, 2023

Related U.S. Application Data

(60) Provisional application No. 63/268,305, filed on Feb. 21, 2022.

(51) Int. Cl.
*A61N 1/02*         (2006.01)

(52) U.S. Cl.
CPC ..................................... *A61N 1/025* (2013.01)

(58) Field of Classification Search
CPC ............................ A61N 1/025; A61N 1/36139
See application file for complete search history.

(56) References Cited

U.S. PATENT DOCUMENTS 4,203,670 A      5/1980   Bromberg
4,400,590 A  *  8/1983   Michelson ........... H04R 25/502
                                              607/57

(Continued)

FOREIGN PATENT DOCUMENTS

WO     WO-2018085664 A1 *   5/2018  ............... A61B 5/24
WO     2021026151 A1     2/2021

OTHER PUBLICATIONS

Instrument, T. (Nov. 2015). LM13700 Dual Operational Transconductance Amplifiers With Linearizing Diodes and Buffers. https://www.ti.com/lit/ds/symlink/lm13700.pdf (Year: 2015).*

(Continued)

*Primary Examiner* — John R Downey
*Assistant Examiner* — Karmel J Webster
(74) *Attorney, Agent, or Firm* — Shumaker & Sieffert, P.A.

(57) ABSTRACT

A system for providing therapy to a patient includes stimulation generation circuitry, sensing circuitry, and processing circuitry. The processing circuitry is configured to cause storage of a first voltage at a first terminal at a first calibration capacitor and storage of a second voltage at a second terminal at a second calibration capacitor. The processing circuitry is configured to switch out a first calibration switch to prevent the first voltage stored at the first calibration capacitor from changing and switch out a second calibration switch to prevent the second voltage stored at the second calibration capacitor from changing and determine, with the sensing circuitry, a sensing signal based on the first voltage offset by a first calibration voltage stored by the first capacitor and based on the second voltage offset by a second calibration voltage stored by the second capacitor.

20 Claims, 20 Drawing Sheets

(56) References Cited

U.S. PATENT DOCUMENTS

| | | | |
|---|---|---|---|
| 4,903,700 | A | 2/1990 | Whigham et al. |
| 4,991,583 | A | 2/1991 | Silvian |
| 5,330,512 | A * | 7/1994 | Hauck .................. A61N 1/3706 |
| | | | 607/28 |
| 9,386,934 | B2 | 7/2016 | Parker et al. |
| 9,950,171 | B2 | 4/2018 | Johanek et al. |
| 10,183,168 | B2 | 1/2019 | Baru et al. |
| 10,278,600 | B2 | 5/2019 | Parker et al. |
| 10,926,092 | B2 | 2/2021 | Esteller et al. |
| 11,129,991 | B2 | 9/2021 | Dinsmoor et al. |
| 2004/0198295 | A1 * | 10/2004 | Nicholls ................ H04B 1/525 |
| | | | 455/296 |
| 2008/0284507 | A1 | 11/2008 | Pertijs et al. |
| 2009/0082691 | A1 | 3/2009 | Denison et al. |
| 2010/0114248 | A1 * | 5/2010 | Donofrio ............... A61N 1/025 |
| | | | 607/63 |
| 2011/0270134 | A1 * | 11/2011 | Skelton .............. A61N 1/36514 |
| | | | 600/595 |
| 2013/0289658 | A1 * | 10/2013 | Denison ............... A61N 1/3787 |
| | | | 607/59 |
| 2015/0119751 | A1 * | 4/2015 | Stanslaski ............ A61N 1/3605 |
| | | | 600/554 |
| 2015/0223710 | A1 | 8/2015 | Cong et al. |
| 2018/0132747 | A1 | 5/2018 | Parker et al. |
| 2018/0205470 | A1 * | 7/2018 | Choi ...................... H04B 17/21 |
| 2018/0221644 | A1 * | 8/2018 | Grill .................. A61N 1/36067 |
| 2018/0243564 | A1 | 8/2018 | Stanslaski et al. |
| 2018/0353760 | A1 | 12/2018 | Bonnet et al. |
| 2019/0190296 | A1 | 6/2019 | Paralikar et al. |
| 2019/0388692 | A1 | 12/2019 | Dinsmoor et al. |
| 2019/0388695 | A1 | 12/2019 | Dinsmoor et al. |
| 2020/0029914 | A1 | 1/2020 | Single |
| 2020/0064252 | A1 * | 2/2020 | Smith ................ G01N 15/1459 |
| 2020/0078592 | A1 * | 3/2020 | Salvia ...................... A61N 1/06 |
| 2020/0085311 | A1 * | 3/2020 | Tzvieli ................... A61B 5/748 |
| 2020/0246626 | A1 * | 8/2020 | Labbe .................. A61N 1/3615 |
| 2020/0266824 | A1 | 8/2020 | Smith et al. |
| 2020/0316382 | A1 * | 10/2020 | Esteller ............... A61N 1/0551 |
| 2021/0008365 | A1 | 1/2021 | Feldman et al. |
| 2021/0187298 | A1 | 6/2021 | Dinsmoor et al. |
| 2021/0346700 | A1 * | 11/2021 | Wilder .............. A61N 1/36139 |
| 2022/0008731 | A1 | 1/2022 | Dinsmoor et al. |
| 2023/0264014 | A1 | 8/2023 | Corey et al. |
| 2024/0009463 | A1 | 1/2024 | Dinsmoor et al. |

OTHER PUBLICATIONS

U.S. Appl. No. 17/654,695, filed Mar. 14, 2022, naming inventors Smith et al.

Extended Search Report from counterpart European Application No. 23157541.6 dated Jul. 6, 2023, 5 pp.

* cited by examiner

100

102

106

132A    132B 108A    108B

110

EXTERNAL
PROGRAMMER
150

500

ANY17 ELECTRODES CAN BE
SELECTED AS STIMULUS PAIR

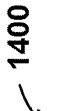
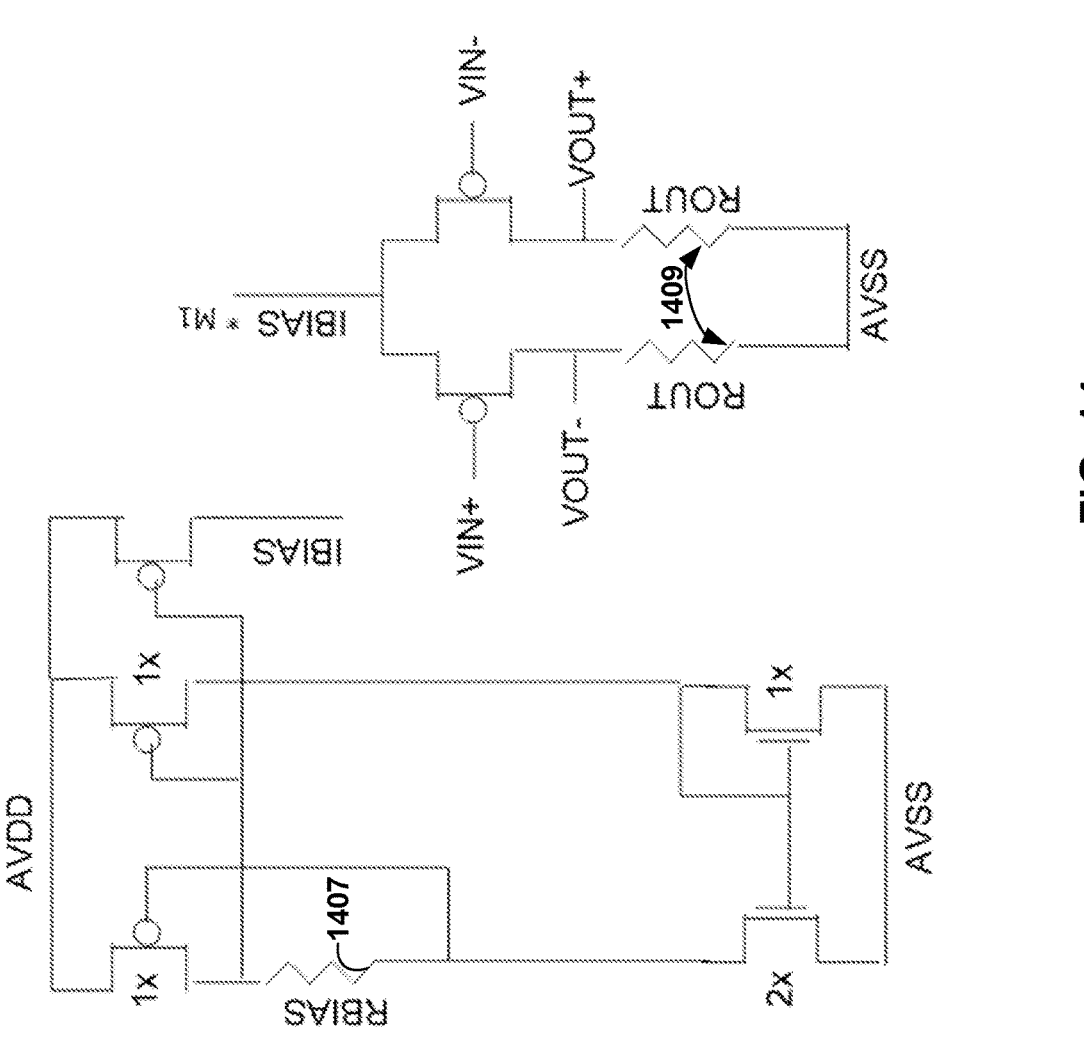
FIG. 14

In the z-domain, an additive linear artifact is described by 2 poles at 1 on the unit circle Any filter operation that has 2 zeros at 1 on the unit circle, removes the additive linear artifact. Any resulting measurement is invariant to the presence of the artifact.

One solution set for invariant filter $f(z) = flip(z)(1 - z^{-1})(1 - z^{-k})$

Amplitude = Max derivative between P2,N1 -
Min derivative between P2,B2

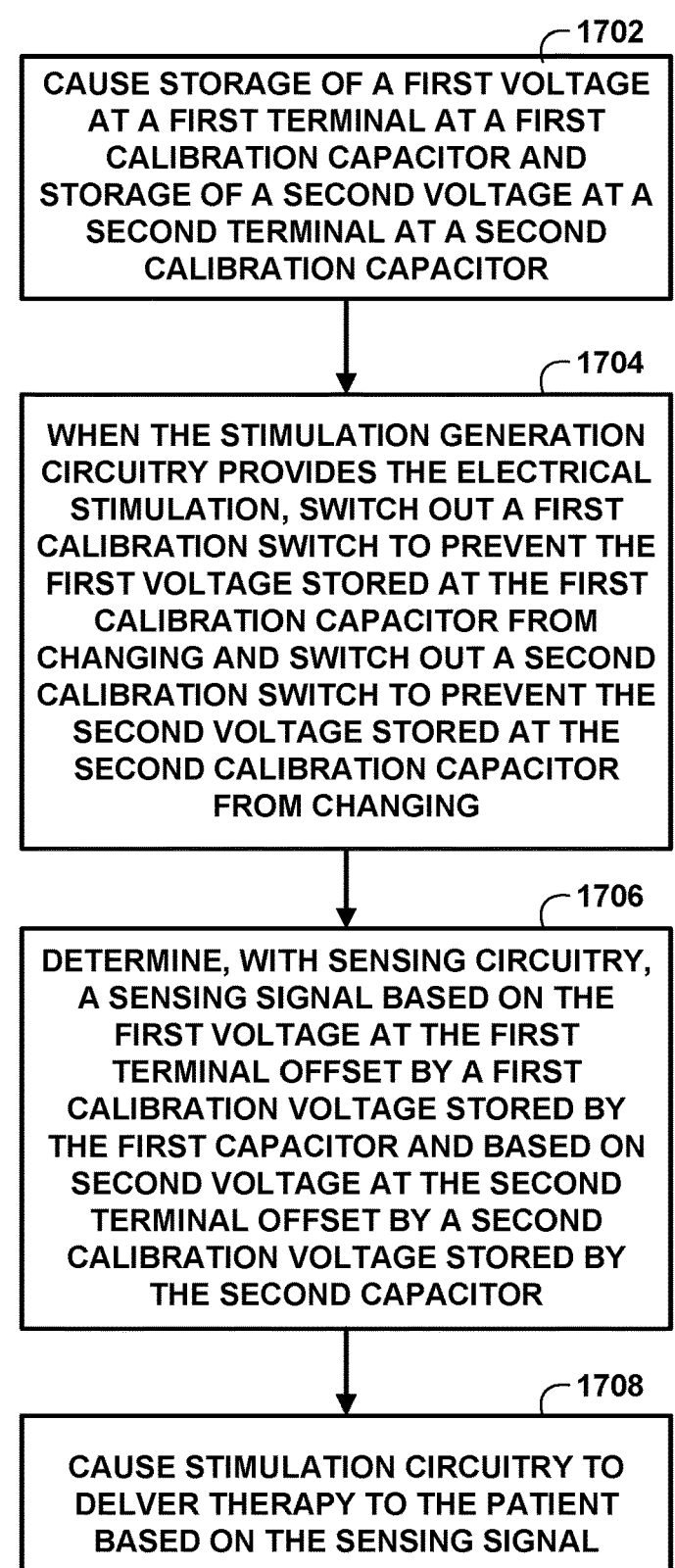

1702

CAUSE STORAGE OF A FIRST VOLTAGE AT A FIRST TERMINAL AT A FIRST CALIBRATION CAPACITOR AND STORAGE OF A SECOND VOLTAGE AT A SECOND TERMINAL AT A SECOND CALIBRATION CAPACITOR

1704

WHEN THE STIMULATION GENERATION CIRCUITRY PROVIDES THE ELECTRICAL STIMULATION, SWITCH OUT A FIRST CALIBRATION SWITCH TO PREVENT THE FIRST VOLTAGE STORED AT THE FIRST CALIBRATION CAPACITOR FROM CHANGING AND SWITCH OUT A SECOND CALIBRATION SWITCH TO PREVENT THE SECOND VOLTAGE STORED AT THE SECOND CALIBRATION CAPACITOR FROM CHANGING

1706

DETERMINE, WITH SENSING CIRCUITRY, A SENSING SIGNAL BASED ON THE FIRST VOLTAGE AT THE FIRST TERMINAL OFFSET BY A FIRST CALIBRATION VOLTAGE STORED BY THE FIRST CAPACITOR AND BASED ON SECOND VOLTAGE AT THE SECOND TERMINAL OFFSET BY A SECOND CALIBRATION VOLTAGE STORED BY THE SECOND CAPACITOR

1708

CAUSE STIMULATION CIRCUITRY TO DELVER THERAPY TO THE PATIENT BASED ON THE SENSING SIGNAL

FIG. 17

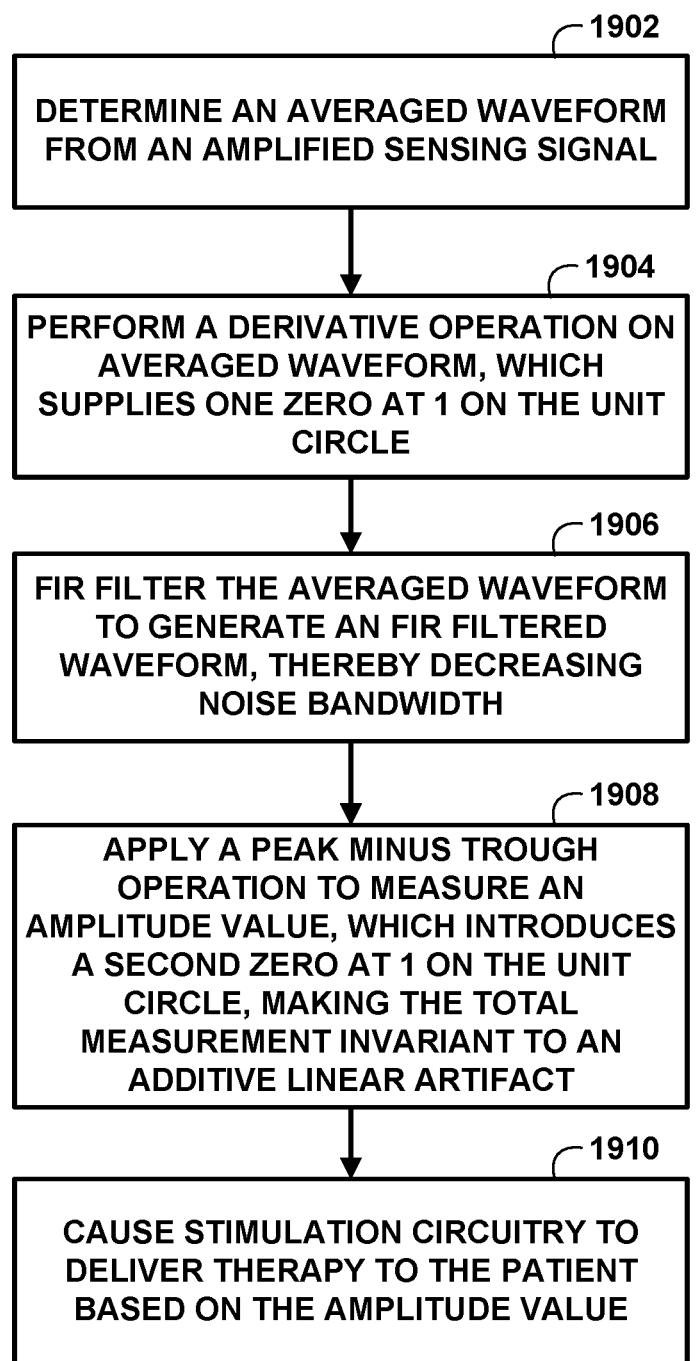

1902

DETERMINE AN AVERAGED WAVEFORM
FROM AN AMPLIFIED SENSING SIGNAL

1904

PERFORM A DERIVATIVE OPERATION ON
AVERAGED WAVEFORM, WHICH
SUPPLIES ONE ZERO AT 1 ON THE UNIT
CIRCLE

1906

FIR FILTER THE AVERAGED WAVEFORM
TO GENERATE AN FIR FILTERED
WAVEFORM, THEREBY DECREASING
NOISE BANDWIDTH

1908

APPLY A PEAK MINUS TROUGH
OPERATION TO MEASURE AN
AMPLITUDE VALUE, WHICH INTRODUCES
A SECOND ZERO AT 1 ON THE UNIT
CIRCLE, MAKING THE TOTAL
MEASUREMENT INVARIANT TO AN
ADDITIVE LINEAR ARTIFACT

1910

CAUSE STIMULATION CIRCUITRY TO
DELIVER THERAPY TO THE PATIENT
BASED ON THE AMPLITUDE VALUE

FIG. 19

SENSING EVOKED COMPOUND ACTION POTENTIAL (ECAP)

This application claims the benefit of U.S. Provisional Patent Application No. 63/268,305, filed 21 Feb. 2022, the entire contents of which is incorporated herein by reference.

TECHNICAL FIELD

This disclosure generally relates to electrical stimulation, and more specifically, control of electrical stimulation.

BACKGROUND

Medical devices may be external or implanted and may be used to deliver electrical stimulation to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively. Electrical stimulation often results in an evoked compound action potential (ECAP) from nerves within the patient.

SUMMARY

In general, systems, devices, and techniques are described herein for calibrating sensing circuitry for generating a sensing signal, such as an evoked action potential (ECAP) signal or brain resonance signals (e.g., ERNA), to help to provide electrical stimulation therapy to a patient. An ECAP signal may refer to a measure of the nerve tissue's response to stimulation. For example, in response to a stimulation, a nerve generates an ECAP signal, and the parameters of the ECAP signal, such as an amplitude value, may be a function of how much the nerve responded to the stimulation. Medical devices can provide more effective therapy by adjusting an amount of stimulation based on sensed ECAP signals.

In one example, a system for providing therapy to a patient includes stimulation generation circuitry configured to provide electrical stimulation to the patient, sensing circuitry configured to sense a first voltage at a first terminal and to sense a second voltage at a second terminal, and processing circuitry electrically connected to the sensing circuitry and stimulation generation circuitry. The processing circuitry is configured to, when the stimulation generation circuitry does not provide the electrical stimulation, cause storage of the first voltage at the first terminal at a first calibration capacitor and storage of the second voltage at the second terminal at a second calibration capacitor. The processing circuitry is further configured to, after the first voltage is stored at the first calibration capacitor and the second voltage is stored at the second calibration capacitor and when the stimulation generation circuitry provides the electrical stimulation, switch out a first calibration switch to prevent the first voltage stored at the first calibration capacitor from changing and switch out a second calibration switch to prevent the second voltage stored at the second calibration capacitor from changing. The processing circuitry is configured to, while the first calibration switch is switched out and the second calibration switch is switched out and when the stimulation generation circuitry does not provide the electrical stimulation, determine, with the sensing circuitry, a sensing signal based on the first voltage at the first terminal offset by a first calibration voltage stored by the first capacitor and based on second voltage at the second terminal offset by a second calibration voltage stored by the second capacitor. The processing circuitry is configured to provide, with the stimulation generation circuitry, the therapy to the patient based on the sensing signal.

In another example, a method includes, when stimulation generation circuitry does not provide the electrical stimulation, cause, by processing circuitry, storage of a first voltage at a first terminal of sensing circuitry at a first calibration capacitor and storage of a second voltage at a second terminal of the sensing circuitry at a second calibration capacitor and after causing the storage of the first voltage at the first calibration capacitor and causing the storage of the second voltage at the second calibration capacitor and when the stimulation generation circuitry provides the electrical stimulation, switching out, by the processing circuitry, a first calibration switch to prevent the first voltage stored at the first calibration capacitor from changing and switching out, by the processing circuitry, a second calibration switch to prevent the second voltage stored at the second calibration capacitor from changing. The method further includes, while the first calibration switch is switched out and the second calibration switch is switched out and when the stimulation generation circuitry does not provide the electrical stimulation, determining, by the processing circuitry, a sensing signal based on the first voltage at the first terminal offset by a first calibration voltage stored by the first capacitor and based on second voltage at the second terminal offset by a second calibration voltage stored by the second capacitor and causing, by the processing circuitry, the stimulation generation circuitry to deliver the therapy to the patient based on the sensing signal.

In one example, a medical device includes stimulation generation circuitry configured to provide electrical stimulation to the patient, sensing circuitry configured to sense a first voltage at a first terminal and to sense a second voltage at a second terminal, and processing circuitry electrically connected to the sensing circuitry and stimulation generation circuitry. The processing circuitry is configured to, when the stimulation generation circuitry does not provide the electrical stimulation, cause storage of the first voltage at the first terminal at a first calibration capacitor and cause storage of the second voltage at the second terminal at a second calibration capacitor, and after the first voltage is stored at the first calibration capacitor and the second voltage is stored at the second calibration capacitor and when the stimulation generation circuitry provides the electrical stimulation, switch out a first calibration switch to prevent the first voltage stored at the first calibration capacitor from changing and switch out a second calibration switch to prevent the second voltage stored at the second calibration capacitor from changing. The processing circuitry is further configured to, while the first calibration switch is switched out and the second calibration switch is switched out and when the stimulation generation circuitry does not provide the electrical stimulation, determine, with the sensing circuitry, a sensing signal based on the first voltage at the first terminal offset by a first calibration voltage stored by the first capacitor and based on second voltage at the second terminal offset by a second calibration voltage stored by the second capacitor and cause the stimulation generation circuitry to deliver the therapy to the patient based on the sensing signal.

In another example, a system for providing therapy to a patient includes stimulation generation circuitry configured to provide electrical stimulation to the patient, sensing circuitry configured to sense a sensing signal, and processing circuitry electrically connected to the sensing circuitry and stimulation generation circuitry. The system further includes amplifier circuitry configured to receive the sensing signal from the sensing circuitry, amplify, using a transconductance amplifier, the sensing signal to generate a first amplified sensing signal, and when the stimulation generation circuitry provides the electrical stimulation, block the first amplified sensing signal from being received at an input of a second stage amplifier. The amplifier circuitry is further configured to, when the stimulation generation circuitry does not provide the electrical stimulation, allow the first amplified sensing signal to be received at the input of the second stage amplifier and amplify, using the second stage amplifier, the first amplified sensing signal, to generate a second amplified signal. The processing circuitry is configured to cause the stimulation generation circuitry to deliver the therapy based on the second amplified sensing signal.

In one example, a system for providing therapy to a patient includes stimulation generation circuitry configured to provide electrical stimulation to the patient, sensing circuitry configured to sense a sensing signal, and processing circuitry electrically connected to the sensing circuitry and stimulation generation circuitry. The processing circuitry is configured to receive the sensing signal from the sensing circuitry and amplify, using a transconductance amplifier, the sensing signal to generate a first amplified sensing signal. The processing circuitry is further configured to, when the stimulation generation circuitry provides the electrical stimulation, block the first amplified sensing signal from being received at an input of a second stage amplifier. The processing circuitry is further configured to, when the stimulation generation circuitry does not provide the electrical stimulation, allow the first amplified sensing signal to be received at the input of the second stage amplifier. The processing circuitry is further configured to amplify, using the second stage amplifier, the first amplified sensing signal, to generate a second amplified signal. The processing circuitry is configured to cause the stimulation generation circuitry to deliver the therapy based on the second amplified sensing signal.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages of the techniques will be apparent from the description and drawings, and from the claims.

BRIEF DESCRIPTION OF DRAWINGS

FIG. 14 is a circuit diagram illustrating an example transconductance amplifier, in accordance with one or more techniques of this disclosure.

FIG. 17 is a flowchart illustrating an example operation for calibrating sensing circuitry of the IMD of FIG. 1, in accordance with one or more techniques of this disclosure.

FIG. 19 is a flowchart illustrating an example operation for feature extraction, in accordance with one or more techniques of this disclosure.

DETAILED DESCRIPTION

The disclosure describes examples of medical devices, systems, and techniques for calibrating sensing circuitry of medical devices configured to provide electrical stimulation therapy. Electrical stimulation therapy is typically delivered to a target tissue (e.g., nerves of the spinal cord or muscle) of a patient via two or more electrodes. The two or more electrodes may deliver control pulses configured to elicit an evoked compound action potential (ECAP) signal from nerve tissue of a patient, or deliver informed pulses config-ured to deliver therapy to the patient. In this disclosure, "control pulses" may be stimulation pulses that are used to elicit the ECAP signal. The control pulses may provide therapeutic effect, but need not necessarily provide thera-peutic effect. "Informed pulses" may be stimulation pulses that provide therapeutic effect. Informed pulses may be "informed" in the sense that the parameters of the informed pulses (e.g., an amplitude, a pulse width, or a frequency) may be based on the sensing of the ECAP signal that was generated due to the control pulses. The informed pulses may be considered as providing governing therapy or gov-erned therapy. Governing therapy or governed therapy may indicate that the stimulation pulses are for effective therapy.

Parameters of the electrical stimulation therapy (e.g., an electrode combination, a voltage amplitude, a current ampli-tude, a pulse width, or a pulse frequency) may be selected by a clinician and/or the patient to provide relief from various symptoms, such as pain, nervous system disorders, muscle disorders, etc. In addition, parameters of the electrical stimu-lation therapy (e.g., informed pulses) may be adjusted in response to a measured ECAP. In order to accurately mea-sure ECAP and provide more effective therapy, sensing circuitry configured to sense ECAP may be effectively calibrated.

This disclosure describes an amplifier (e.g., a bio-ampli-fier) and processing circuitry to measure an amplitude value of an evoked compound action potential (ECAP) of the human spinal cord. This low power system can detect very small signals (e.g., 10 μVpp (0-4.5 kHz)), very shortly (e.g., less than 200 us) after a large stimuli (e.g., about 10 V) using a medical device (e.g., an implantable device) that has no appreciable DC pathway to the body, which may help to maximize patient safety. The measured amplitude values may correlate to the amount of tissue captured by electrical stimulus, which varies with body position and other factors, allowing for optimal therapy level control.

Figure 1:
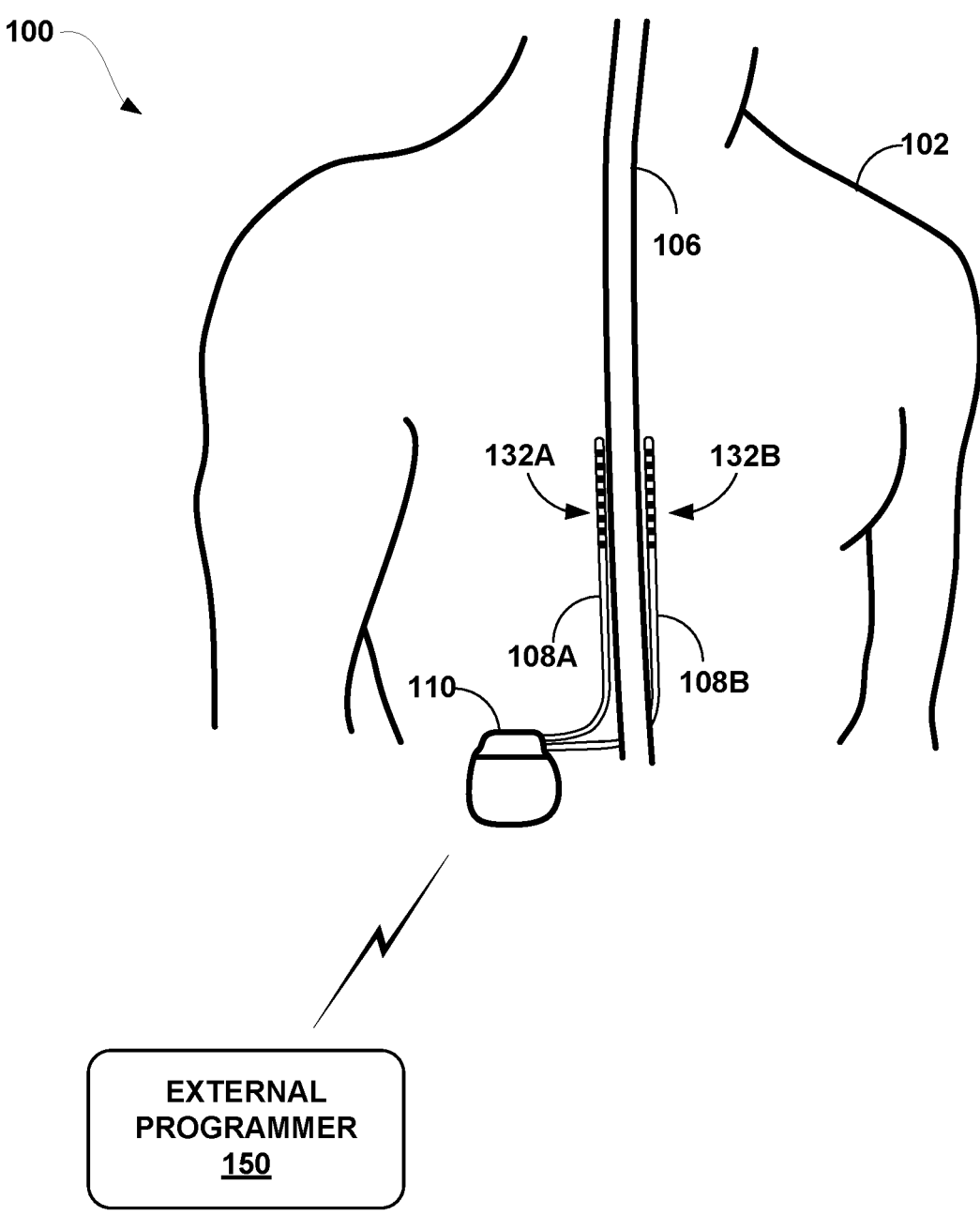
FIG. 1 is a conceptual diagram illustrating an example system that includes an implantable medical device (IMD) according to the techniques of the disclosure.

FIG. 1 is a conceptual diagram illustrating an example system 100 that includes an IMD 110 according to the techniques of the disclosure. Although the techniques described in this disclosure are generally applicable to a variety of medical devices including external devices and IMDs, application of such techniques to IMDs and, more particularly, implantable electrical stimulators (e.g., neuro-stimulators) will be described for purposes of illustration. More particularly, the disclosure will refer to an implantable SCS system for purposes of illustration, but without limita-tion as to other types of medical devices or other therapeutic applications of medical devices.

As shown in FIG. 1, system 100 includes an IMD 110, leads 108A and 108B, and external programmer 150 shown in conjunction with a patient 102, who is a human patient. In the example of FIG. 1, IMD 110 is an implantable electrical stimulator that is configured to generate and deliver electrical stimulation therapy to patient 102 via one or more electrodes of electrodes 132A and/or 132B (collec-tively, "electrodes 132") of leads 108A and/or 108B (col-lectively, "leads 108"), e.g., for relief of chronic pain or other symptoms. In other examples, IMD 110 may be coupled to a single lead carrying multiple electrodes or more than two leads each carrying multiple electrodes. In some examples, the stimulation signals, or pulses (e.g., control pulses), may be configured to elicit detectable ECAP signals that IMD 110 may use to determine the posture state occupied by patient 102 and/or determine how to adjust one or more parameters that define stimulation therapy. The control pulses may provide therapeutic effect, but in one or more examples, the control pulses may not provide thera-peutic effect. IMD 110 may be configured to delivered informed pulses for providing therapeutic effect. The informed pulses may be "informed" because the parameters of the informed pulses may be based on the ECAP signal generated from the delivery of control pulses. The informed pulses may be considered as providing governed therapy. Governing therapy may indicate that the stimulation pulses are for effective therapy. The control pulses may be "con-trol" because the delivery of the control pulses is used to control the parameters for the informed pulses.

IMD 110 may be a chronic electrical stimulator that remains implanted within patient 102 for weeks, months, or even years. In other examples, IMD 110 may be a temporary, or trial, stimulator used to screen or evaluate the efficacy of electrical stimulation for chronic therapy. In one example, IMD 110 is implanted within patient 102. In some examples, a medical device, configured to perform techniques similar to IMD 110, may be an external device coupled to percu-taneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 102. In this example, IMD 110 may be constructed with a biocompatible housing, such as titanium or stainless steel, or a polymeric material such as silicone, polyurethane, or a liquid crystal polymer, and surgically implanted at a site in patient 102 near the pelvis, abdomen, or buttocks. In other examples, IMD 110 may be implanted within other suitable sites within patient 102, which may depend, for example, on the target site within patient 102 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 102 via one or more electrodes 132 of implantable leads 108. In the example of FIG. 1, leads 108 carry electrodes 132 that are placed adjacent to the target tissue of spinal cord 106. One or more of electrodes 132 may be disposed at a distal tip of a lead 108 and/or at other positions at intermediate points along the lead. Leads 108 may be implanted and coupled to IMD 110. Electrodes 132 may transfer electrical stimulation generated by an electrical stimulation generator in IMD 110 to tissue of patient 102. Although leads 108 may each be a single lead, lead 108 may include a lead extension or other segments that may aid in implantation or positioning of lead 108. In some examples, IMD 110 may be a leadless stimulator with one or more arrays of electrodes arranged on a housing of the stimulator rather than leads that extend from the housing. In addition, in some examples, system 100 may include one lead or more than two leads, each coupled to IMD 110 and directed to similar or different target tissue sites.

Electrodes 132 of leads 108 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a con-tinuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 108 will be described for purposes of illustration.

The deployment of electrodes 132 via leads 108 is described for purposes of illustration, but arrays of electrodes 132 may be deployed in different ways. For example, a housing associated with a leadless stimulator may carry arrays of electrodes 132, e.g., rows and/or columns (or other patterns), to which shifting operations may be applied. Such electrodes 132 may be arranged as surface electrodes, ring electrodes, or protrusions. As a further alternative, electrode arrays may be formed by rows and/or columns of electrodes 132 on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 108 are linear leads having 8 ring electrodes along the axial length of the lead. In another example, electrodes 132 are segmented rings arranged in a linear fashion along the axial length of the lead and at the periphery of the lead.

The stimulation parameter set of a stimulation program that defines the stimulation pulses of electrical stimulation therapy by IMD 110 through the electrodes of leads 108 may include information identifying which electrodes 132 have been selected for delivery of stimulation according to a stimulation program, the polarities of the selected electrodes 132, e.g., an electrode combination for the program, a voltage amplitude, a current amplitude, a pulse frequency, a pulse width, or a pulse shape of stimulation delivered by electrodes 132. These stimulation parameters values that make up the stimulation parameter set that defines pulses may be predetermined parameter values defined by a user and/or automatically determined by system 100 based on one or more factors or user input. Informed pulses may be defined by a set of informed stimulation parameter values and control pulses may be defined by a set of control stimulation parameter values.

Although FIG. 1 is directed to SCS therapy, e.g., used to treat pain, in other examples system 100 may be configured to treat any other condition that may benefit from electrical stimulation therapy. In some examples, system 100 may be configured to provide multimodal stimulation using prime stimulation and base stimulation together. In some examples, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of spinal cord stimulation (SCS), deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 102.

In some examples, lead 108 includes one or more sensors configured to allow IMD 110 to monitor one or more parameters of patient 102, such as patient activity, pressure, temperature, or other characteristics. The one or more sensors may be provided in addition to, or in place of, therapy delivery by lead 108. Rather than or in addition to lead 108 including such sensors, IMD 110 may include such sensors.

IMD 110 may be configured to deliver electrical stimulation therapy (e.g., informed pulses and/or control pulses in the form of a prime pulse train and base pulse train, respectively) to patient 102 via selected combinations of electrodes 132 carried by one or both of leads 108, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated by FIG. 1, the target tissue is tissue proximate spinal cord 106, such as within an intrathecal space or epidural space of spinal cord 106, or, in some examples, adjacent nerves that branch off spinal cord 106.

Leads 108 may be introduced into spinal cord 106 in via any suitable region, such as the thoracic, cervical, or lumbar regions. Stimulation of spinal cord 106 may, for example, prevent pain signals from traveling through spinal cord 106 and to the brain of patient 102. Patient 102 may perceive the interruption of pain signals as a reduction in pain and, therefore, efficacious therapy results. In other examples, stimulation of spinal cord 106 may produce paresthesia which may be reduce the perception of pain by patient 102, and thus, provide efficacious therapy results. In some examples, stimulation of spinal cord 106 or other anatomical structures associated with the spinal cord (e.g., nerves and cells associated with the nervous system) may provide relief from symptoms that may not produce paresthesia. For example, IMD 110 may deliver stimulation with intensities (e.g., amplitude values and/or pulse width values) below a sensory or perception threshold (e.g., sub-threshold stimulation) that reduces pain without paresthesia. In multimodal stimulation, for example, IMD 110 may deliver one pulse train at a higher frequency via one electrode combination and a second pulse train on an interleaved basis with a lower frequency via a second electrode combination, where both pulse trains are delivered at a sub-threshold intensity.

IMD 110 may be configured to generate and deliver electrical stimulation therapy to a target stimulation site within patient 102 via electrodes 132 of leads 108 to patient 102 according to one or more therapy stimulation programs. A therapy stimulation program may generally define informed pulses, but may also define control pulses if the control pulses also contribute to a therapeutic effect. A therapy stimulation program may define values for one or more parameters (e.g., a parameter set) that define an aspect of the therapy delivered by IMD 110 according to that program. For example, a therapy stimulation program that controls delivery of stimulation by IMD 110 in the form of pulses may define a voltage, a current, a pulse width, a pulse rate (e.g., a pulse frequency), an electrode combination, or a pulse shape for stimulation pulses delivered by IMD 110 according to that program. In some examples, one or more therapy stimulation programs define multiple different pulse trains that have different parameter values (e.g., different pulse frequencies, amplitude values, pulse widths, and/or electrode combinations) but are delivered on an interleaved basis to together provide a therapy for the patient.

Furthermore, IMD 110 may be configured to deliver control stimulation to patient 102 via a combination of electrodes 132 of leads 108, alone or in combination with an electrode carried by or defined by an outer housing of IMD 110 in order to detect ECAP signals (e.g., control pulses and/or informed pulses). The tissue targeted by the stimulation may be the same or similar tissue targeted by the electrical stimulation therapy, but IMD 110 may deliver stimulation pulses for ECAP signal detection via the same, at least some of the same, or different electrodes of electrodes 132. Because control stimulation pulses can be delivered in an interleaved manner with informed pulses (e.g., when the pulses configured to contribute to therapy interfere with the detection of ECAP signals or pulse sweeps intended for posture state detection via ECAP signals do not correspond to pulses intended for therapy purposes), a clinician and/or user may select any desired electrode 132 combination for informed pulses (i.e., governed therapy). Like the electrical stimulation therapy, the control stimulation may be in the form of electrical stimulation pulses or continuous waveforms.

For example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. The control pulses may elicit an ECAP signal from the tissue, and IMD 110 may sense the ECAP signal via two or more electrodes 132 on leads 108. In cases where the control stimulation pulses are applied to spinal cord 106, the signal may be sensed by IMD 110 from spinal cord 106.

A user, such as a clinician or patient 102, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control stimulation, such as stimulation pulses that provide electrical stimulation therapy. For example, external programmer 150 may transmit therapy stimulation programs, stimulation parameter adjustments, therapy stimulation program selections, posture states, user input, or other information to control the operation of IMD 110, e.g., by wireless telemetry or wired connection.

In some examples, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 102 and, in many cases, may be a portable device that may accompany patient 102 throughout the patient's daily routine. For example, a patient programmer may receive input from patient 102 when the patient wishes to terminate or change electrical stimulation therapy, or when a patient perceives stimulation being delivered. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this way, a user may program and charge IMD 110 using one device, or multiple devices.

As described herein, information may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, may deliver electrical stimulation therapy (e.g., informed pulses and/or control pulses) according to a plurality of therapy stimulation programs to a target tissue site of the spinal cord 106 of patient 102 via electrodes 132 on leads 108. In some examples, IMD 110 may modify therapy stimulation programs as therapy needs of patient 102 evolve over time. For example, the modification of the therapy stimulation programs may cause the adjustment of at least one parameter of the plurality of stimulation pulses. When patient 102 receives the same therapy for an extended period, the efficacy of the therapy may be reduced. In some cases, parameters of the plurality of stimulation pulses may be automatically (e.g., without user input) updated, for example, by IMD 110, external programmer 150 or another device or cloud system.

Efficacy of electrical stimulation therapy may be indicated by one or more features (e.g., an amplitude value between one or more peaks or an area under the curve of one or more peaks) of an action potential that is evoked by a control pulse delivered by IMD 110 (i.e., a characteristic value of the ECAP signal). Electrical stimulation therapy delivery by leads 108 of IMD 110 may cause neurons within the target tissue to evoke a compound action potential that travels up and down the target tissue, eventually arriving at sensing electrodes of IMD 110 (e.g., electrodes of electrodes 132 that are assigned for sensing). For instance, stimulation may elicit at least one ECAP signal, and ECAP responsive to stimulation may also be a surrogate for the effectiveness of the therapy. The amount of action potential (e.g., number of neurons propagating action potential signals) that are evoked may be based on the various parameters of electrical stimulation pulses such as an amplitude value, a pulse width, a frequency, or a pulse shape (e.g., slew rate at the beginning and/or end of the pulse). The slew rate may define the rate of change of the voltage amplitude value and/or current amplitude value of the control pulse at the beginning and/or end of each control pulse or each phase within the pulse. For example, a very high slew rate indicates a steep or even near vertical edge of the pulse, and a low slew rate indicates a longer ramp up (or ramp down) in the amplitude value of the control pulse. In some examples, these parameters contribute to an intensity of the electrical stimulation. In addition, a characteristic of the ECAP signal (e.g., an amplitude value) may change based on the distance between the stimulation electrodes and the nerves subject to the electrical field produced by the delivered control pulses.

Some example techniques for adjusting stimulation parameter values for stimulation pulses (e.g., informed pulses and/or control pulses that may or may not contribute to therapy for the patient) are based on comparing the value of a characteristic of a measured ECAP signal to a target ECAP characteristic value. In response to delivering a control pulse defined by a set of stimulation parameter values, IMD 110, via two or more electrodes interposed on leads 108, senses electrical potential of tissue of the spinal cord 106 of patient 102 to measure the electrical activity of the tissue. IMD 110 senses ECAP from the target tissue of patient 102, e.g., with electrodes on one or more leads 108 and associated sense circuitry. In some examples, IMD 110 may receive a sensor signal indicative of the ECAP from one or more sensors, e.g., one or more electrodes and circuitry, internal or external to patient 102. Such an example signal may include a sensor signal indicating an ECAP of the tissue of patient 102. Examples of the one or more sensors include one or more sensors configured to measure a compound action potential of patient 102, or a physiological effect indicative of a compound action potential. For example, to measure a physiological effect of a compound action potential, the one or more sensors may be an accelerometer, a pressure sensor, a bending sensor, a sensor configured to detect a posture of patient 102, or a sensor configured to detect a respiratory function of patient 102. In some examples, external programmer 150 may receive a sensor signal indicating a compound action potential in the target tissue of patient 102 and may transmit a notification of the sensor signal to IMD 110.

In the example of FIG. 1, IMD 110 is described as performing a plurality of processing and computing functions. However, external programmer 150 instead may perform one, several, or all of these functions. In this example, IMD 110 functions to relay sensed signals to external programmer 150 for analysis, and external programmer 150 transmits instructions to IMD 110 to adjust the one or more parameters defining the electrical stimulation therapy based on analysis of the sensed signals. For example, IMD 110 may relay the sensed signal indicative of an ECAP to external programmer 150. External programmer 150 may compare the parameter value of the ECAP to the target ECAP characteristic value, and in response to the comparison, external programmer 150 may instruct IMD 110 to adjust one or more stimulation parameter that defines the electrical stimulation informed pulses and, in some examples, control pulses, delivered to patient 102.

In some examples, system 100 may change the target ECAP characteristic value and/or growth rate(s) over a period of time, such as according to a change to a stimulation threshold (e.g., a perception threshold or detection threshold specific for the patient). System 100 may be programmed to change the target ECAP characteristic in order to adjust the intensity of informed pulses (e.g., governed therapy) to provide varying sensations to the patient (e.g., increase or decrease the volume of neural activation). Although system 100 may change the target ECAP characteristic value, received ECAP signals may be used by system 100 to adjust one or more parameter values of the informed pulses and/or control pulses in order to meet the target ECAP characteristic value.

One or more devices within system 100, such as, for example, IMD 110 and/or external programmer 150, may perform various functions as described herein. For example, IMD 110 may include stimulation generation circuitry configured to deliver electrical stimulation, sensing circuitry configured to sense a plurality ECAP signals, and processing circuitry. The processing circuitry may be configured to control the stimulation generation circuitry to deliver a plurality of electrical stimulation pulses (e.g., one or more control pulses) having different amplitude values and control the sensing circuitry to detect, after delivery of each electrical stimulation pulse of the plurality of electrical stimulation pulses, a respective ECAP signal of the plurality of ECAP signals.

In some examples, reference may be made to one or more electrodes of IMD 110 "delivering" therapy. In these instances, stimulation generation circuitry of IMD 110 may be connected to one or more electrodes 132 and configured to deliver the therapy "using" or "on" one or more electrodes 132. In some examples described herein, reference may be made to one or more electrodes 132 of IMD 110 "sensing" ECAP signals. In these instances, sensing circuitry of IMD 110 may be connected to one or more electrodes 132 and configured to sense the ECAP signals "using" or "on" one or more electrodes 132. A different set (e.g., pair) of one or more electrodes 132 may be used for delivering therapy than a set (e.g., pair) of one or more electrodes 132 may be used for sensing ECAP signals. While the above refers to ECAP signals, similar techniques may be used for other sensing signals. In some examples, reference may be made to certain recharge states (e.g., active recharge or passive recharge) as "on" one or more electrodes 132 of IMD 110. In these instances, circuitry connected to one or more electrodes 132 may be "in" the certain recharge state.

In the example of FIG. 1, IMD 110 is described as performing a plurality of processing and computing functions. However, external programmer 150 instead may perform one, several, or all of these functions. In this example, IMD 110 may relay sensed signals to external programmer 150 for analysis and external programmer 150 may transmit instructions to IMD 110 to adjust the one or more parameters defining the electrical stimulation signal based on analysis of the sensed signals. For example, IMD 110 may relay the sensed signal indicative of an ECAP to external programmer 150. External programmer 150 may compare the parameter value of the ECAP to the target ECAP characteristic value, and in response to the comparison, external programmer 150 may instruct IMD 110 to adjust one or more parameters that define the electrical stimulation signal.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitude values. Therefore, electrical stimulation in the form of a non-pulse signal may be a continuous signal that may have a sinusoidal waveform or other continuous waveform.

In some examples, sensing circuitry of IMD 110 may be coupled to control electrodes of one or more electrodes 132 and governing electrodes of one or more electrodes 132. The control electrodes may be configured to deliver control pulses to patient tissue that elicit ECAP signals from the tissue of patient 102. The governing electrodes may be configured to deliver governed therapy (e.g., informed pulses) to patient tissue that provide therapy to patient 102. The sensing circuitry may include one or more amplifiers configured to amplify ECAP signals within the circuitry for more accurate sensing of the ECAP signals. The sensing circuitry may also include processing circuitry configured to enter an active recharge state on the control electrodes and, subsequent to entering an active recharge state, enter a passive recharge state on the control electrodes. The active recharge state and passive recharge state are explained with more specificity below. The processing circuitry may also be configured to calibrate, or auto-zero the operational amplifier of sensing circuitry while the control electrodes are in the passive recharge state.

Figure 2:
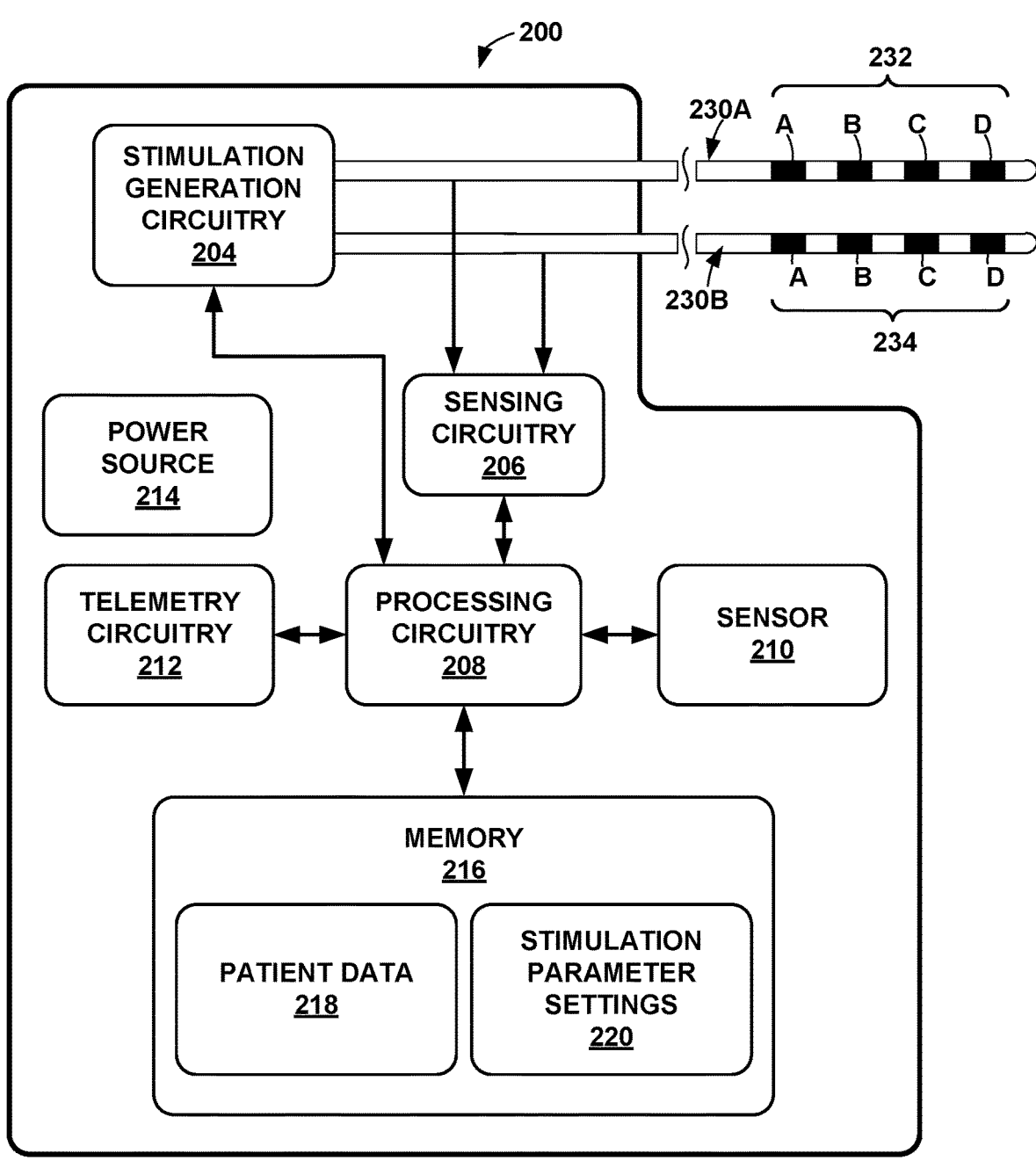
FIG. 2 is a block diagram of the example IMD of FIG. 1, in accordance with one or more techniques of this disclosure.

FIG. 2 is a block diagram of the example IMD of FIG. 1. IMD 200 may be an example of IMD 110 of FIG. 1. In the example shown in FIG. 2, IMD 200 includes stimulation generation circuitry 204, sensing circuitry 206, processing circuitry 208, sensor 210, telemetry circuitry 212, power source 214, and memory 216. Each of these circuits may be or include programmable or fixed function circuitry can perform the functions attributed to respective circuitry. For example, processing circuitry 208 may include fixed-function or programmable circuitry, stimulation generation circuitry 204 may include circuitry can generate electrical stimulation signals such as pulses or continuous waveforms on one or more channels, sensing circuitry 206 may include sensing circuitry for sensing signals, and telemetry circuitry 212 may include telemetry circuitry for transmission and reception of signals. Memory 216 may store computer-readable instructions that, when executed by processing circuitry 208, cause IMD 200 to perform various functions described herein. Memory 216 may be a storage device or other non-transitory medium.

In the example shown in FIG. 2, memory 216 may store patient data 218, which may include anything related to the patient such as one or more patient postures, an activity level, or a combination of patient posture and activity level. Memory 216 may store stimulation parameter settings 220 within memory 216 or separate areas within memory 216. Each stored stimulation parameter setting 220 defines values for one or more sets of electrical stimulation parameters (e.g., an informed stimulation parameter set and a control stimulation parameter set, or parameters for other pulse trains). Stimulation parameter settings 220 may also include additional information such as instructions regarding delivery of electrical stimulation signals based on stimulation parameter relationship data, which can include relationships between two or more stimulation parameters based upon data from electrical stimulation signals delivered to patient 102 or data transmitted from external programmer 104. The stimulation parameter relationship data may include measurable aspects associated with stimulation, such as an ECAP characteristic value.

Accordingly, in some examples, stimulation generation circuitry 204 may generate electrical stimulation signals (e.g., informed pulses and/or control pulses) in accordance with the electrical stimulation parameters noted above. Other ranges of stimulation parameter values may also be useful and may depend on the target stimulation site within patient 102. While stimulation pulses are described, stimulation signals may be of any form, such as continuous-time signals (e.g., sine waves or cosine waves) or the like.

Sensing circuitry 206 may be configured to monitor signals from any combination of electrodes 232, 234. In some examples, sensing circuitry 206 includes one or more amplifiers, filters, and analog-to-digital converters. Sensing circuitry 206 may be used to sense physiological signals, such as ECAP. In some examples, sensing circuitry 206 detects ECAP from a particular combination of electrodes 232, 234. In some examples, the particular combination of electrodes for sensing ECAP includes different electrodes than a set of electrodes 232, 234 used to deliver control stimulation pulses and/or informed stimulation pulses. In some examples, the particular combination of electrodes used for sensing ECAP includes at least one of the same electrodes as a set of electrodes used to deliver informed and/or control stimulation pulses to patient 102. Sensing circuitry 206 may provide signals to an analog-to-digital converter (ADC), for conversion into a digital signal for processing, analysis, storage, or output by processing circuitry 208.

Processing circuitry 208 may include any one or more of a microprocessor, a controller, a digital signal processor (DSP), an application specific integrated circuit (ASIC), a field-programmable gate array (FPGA), discrete logic circuitry, or any other processing circuitry can provide the functions attributed to processing circuitry 208 herein may be embodied as firmware, hardware, software, or any combination thereof. Processing circuitry 208 may control stimulation generation circuitry 204 to generate electrical stimulation signals according to stimulation parameter settings 220 stored in memory 216 to apply stimulation parameter values, such as, for example, a pulse amplitude value, a pulse width, a pulse frequency, and/or a waveform shape of each of the electrical stimulation signals.

In the example of FIG. 2, set of electrodes 232 includes electrodes 232A, 232B, 232C, and 232D, and the set of electrodes 234 includes electrodes 234A, 234B, 234C, and 234D. In some examples, a single lead may include all eight electrodes 232 and 234 along a single axial length of the lead. Processing circuitry 208 also controls stimulation generation circuitry 204 to generate and apply the electrical stimulation signals to selected combinations of electrodes 232, 234. In some examples, stimulation generation circuitry 204 includes a switch circuit that may couple stimulation signals to selected conductors within leads 230, which, in turn, may deliver the stimulation signals across selected electrodes 232, 234. Such a switch circuit may be a switch array, switch matrix, multiplexer, or any other type of switch circuitry can selectively couple stimulation energy to selected electrodes 232, 234 and to selectively sense bioelectrical neural signals of a spinal cord of the patient (not shown in FIG. 2) with selected electrodes 232, 234.

As shown, stimulation generation circuitry 204 may not include a switch circuit. In these examples, stimulation generation circuitry 204 may include a plurality of pairs of voltage sources, current sources, voltage sinks, or current sinks connected to each of electrodes 232, 234 such that each pair of electrodes has a unique signal circuit. In other words, in these examples, each of electrodes 232, 234 may be independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 204 via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 204 and processing circuitry 208 in FIG. 2, in some examples, sensing circuitry 206 may be in a separate housing from IMD 200 and may communicate with processing circuitry 208 via wired or wireless communication techniques.

In some examples, one or more of electrodes 232 and 234 may be suitable for sensing ECAP. For instance, electrodes 232 and 234 may sense the voltage amplitude of a portion of the ECAP signals, where the sensed voltage amplitude is a characteristic the ECAP signal.

Memory 216 may be configured to store information within IMD 200 during operation. Memory 216 may include a computer-readable storage medium or computer-readable storage device. In some examples, memory 216 includes one or more of a short-term memory or a long-term memory. Memory 216 may include, for example, random access memories (RAM), dynamic random-access memories (DRAM), static random-access memories (SRAM), magnetic discs, optical discs, flash memories, or forms of electrically programmable memories (EPROM) or electrically erasable and programmable memories (EEPROM). In some examples, memory 216 is used to store data indicative of instructions for execution by processing circuitry 208. As discussed herein, memory 216 can store patient data 218, stimulation parameter settings 220, and control policy data 224.

Sensor 210 may include one or more sensing elements that sense values of a respective patient parameter. As described, electrodes 232 and 234 may be the electrodes that sense, via sensing circuitry 206, a value of the ECAP indicative of a target stimulation intensity. Sensor 210 may include one or more accelerometers, optical sensors, chemical sensors, temperature sensors, pressure sensors, or any other types of sensors. Sensor 210 may output patient parameter values that may be used as feedback to control delivery of electrical stimulation signals. IMD 200 may include additional sensors within the housing of IMD 200 and/or coupled via one of leads 108 or other leads. In addition, IMD 200 may receive sensor signals wirelessly from remote sensors via telemetry circuitry 212, for example. In some examples, one or more of these remote sensors may be external to patient (e.g., carried on the external surface of the skin, attached to clothing, or otherwise positioned external to the patient). In some examples, signals from sensor 210 may indicate a posture state (e.g., sleeping, awake, sitting, standing, or the like), and processing circuitry 208 may select target and/or threshold ECAP characteristic values according to the indicated posture state.

Telemetry circuitry 212 supports wireless communication between IMD 200 and an external programmer (not shown in FIG. 2) or another computing device under the control of processing circuitry 208. Processing circuitry 208 of IMD 200 may receive, as updates to programs, values for various stimulation parameters such as an amplitude value and/or an electrode combination (e.g., for informed and/or control pulses), from the external programmer via telemetry circuitry 212. Updates to stimulation parameter settings 220 and input efficacy threshold settings 226 may be stored within memory 216. Telemetry circuitry 212 in IMD 200, as well as telemetry circuits in other devices and systems described herein, such as the external programmer, may accomplish communication by radiofrequency (RF) communication techniques. In addition, telemetry circuitry 212 may communicate with an external medical device programmer (not shown in FIG. 2) via proximal inductive interaction of IMD 200 with the external programmer. The external programmer may be one example of external programmer 104 of FIG. 1. Accordingly, telemetry circuitry 212 may send information to the external programmer on a continuous basis, at periodic intervals, or upon request from IMD 110 or the external programmer.

Power source 214 may deliver operating power to various components of IMD 200. Power source 214 may include a rechargeable or non-rechargeable battery and a power generation circuit to produce the operating power. Recharging may be accomplished through proximal inductive interaction between an external charger and an inductive charging coil within IMD 200. In other examples, traditional primary cell batteries may be used. In some examples, processing circuitry 208 may monitor the remaining charge (e.g., voltage) of power source 214 and select stimulation parameter values that may deliver similarly effective therapy at lower power consumption levels when needed to extend the operating time of power source 214.

Stimulation generation circuitry 204 of IMD 200 may receive, via telemetry circuitry 212, instructions to deliver electrical stimulation according to stimulation parameter settings 220 to a target tissue site of the spinal cord of the patient via a plurality of electrode combinations of electrodes 232, 234 of leads 230 and/or a housing of IMD 200. Each electrical stimulation signal may elicit an ECAP signal that is sensed by sensing circuitry 206 via electrodes 232 and 234. Processing circuitry 208 may receive, via an electrical signal sensed by sensing circuitry 206, information indicative of an ECAP signal (e.g., a numerical value indicating a characteristic of the ECAP in electrical units such as voltage or power) produced in response to the electrical stimulation signal(s). Stimulation parameter settings 220 may be updated according to the ECAP recorded at sensing circuitry 206. While the above discussion refers to an ECAP signal, some examples, may be directed to other sensing signals.

Figure 3:
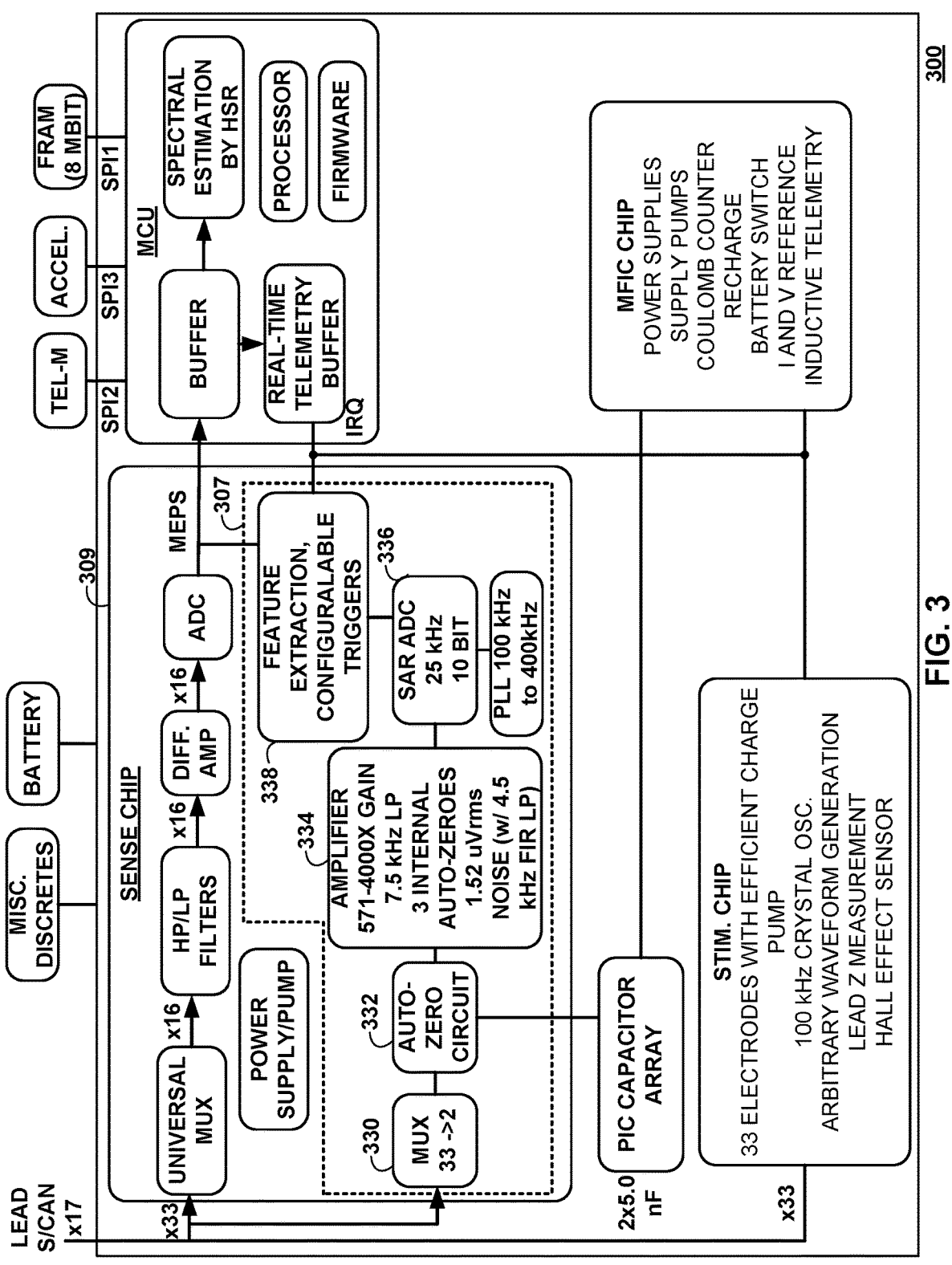
FIG. 3 is a conceptual diagram illustrating an example circuit for the IMD of FIG. 1, in accordance with one or more techniques of this disclosure.

FIG. 3 is a conceptual diagram illustrating an example circuit 300 for the IMD of FIG. 1, in accordance with one or more techniques of this disclosure. In this example, sensor circuitry 307 of sense chip 309 may be configured to detect a sense signal (e.g., an ECAP signal). For example, sensor circuitry 307 may use a multiplexer 330 (also referred to herein as "MUX 330") to select a pair of electrodes. Auto-zero circuit 332 may be configured to perform auto-zero techniques, which are described in further details in FIGS. 4 and 10. Amplifier 334 may be configured to amplify the sense signal generated by auto-zero circuit 332, examples of which are discussed with respect to FIG. 5. Successive-approximation-register analog-to-digital converter 336 (also referred to herein as "SAR ADC 336") may represent the sensing signal as a digital value. Feature extraction and configurable triggers unit 338 may be configured to extract features (e.g., ECAP features) from the digitized sensing signal output by SAR ADC 336, examples of which are discussed with respect to FIGS. 15A, 15B, 16.

Figure 4:
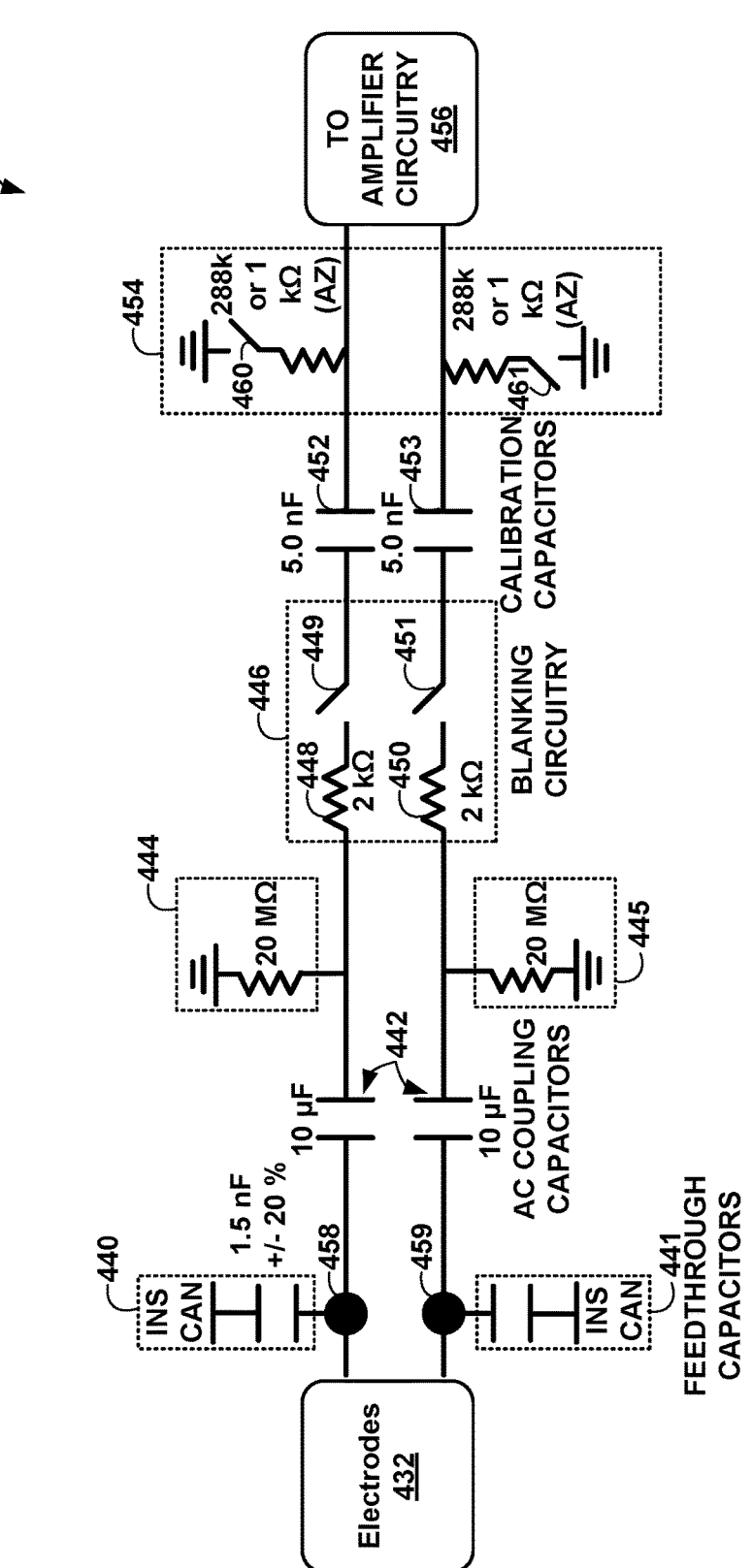
FIG. 4 is a conceptual diagram illustrating an example analog circuit for determining a sensor signal, in accordance with one or more techniques of this disclosure.

FIG. 4 is a conceptual diagram illustrating an example analog circuit 400 for determining a sensor signal, in accordance with one or more techniques of this disclosure. Any of one or more electrodes 132 (e.g., 17 electrodes) at the device level can be selected as the sensing pair of electrodes 432. For the channels not being sensed, the MUX/Blanking switches may be left open (e.g., NMOS gate at ground), always disconnecting them from calibration capacitors 452, 453 (e.g., the 2 shared 5.0 nF capacitors). Only the selected sensing pair of electrodes 432 is shown in the below diagram for example purposes only.

Sensing circuitry 206 of FIG. 2 may be configured to sense an ECAP signal from patient tissue. Sensing circuitry 206 may include circuit 400 prior to outputting to amplifier circuitry 456, where amplifier circuitry 456 may be configured to amplify a sensing signal (e.g., an ECAP signal) sensed by sensing circuitry 206. Circuit 400 may include electrodes 432, feedthrough capacitors 440, 441, AC coupling capacitors 442, grounding circuitry 444, 445, blanking circuitry 446, calibration capacitors 452, 453, and auto-zero circuitry 454. Grounding circuitry 444, 445 may provide a high impedance grounding of circuit 400 to ground (e.g., a battery ground).

Electrodes 432 may be examples of electrodes 232, 234 of FIG. 2 and may be coupled to circuit 400. For example, electrodes 432 may rest against the patient tissue (e.g., spinal cord) of patient 102. Electrodes 432 may include control electrodes configured to deliver a control pulse to the patient tissue that elicits an ECAP signal from patient tissue. Electrodes 432 may also include governing electrodes configured to deliver governed therapy (e.g., informed pulses) to patient tissue that provides therapy to patient 102. One or more electrodes 432 may collect an ECAP signal from patient tissue and provide an electrical signal to the sensing circuitry of circuit 400 representing an amplitude value for the ECAP signal.

As the stimulation generation circuitry 204 of the IMD 200 provides therapy to patient tissue, AC coupling capacitors 442 may prevent accumulated charge on electrodes 432 from impacting the patient by holding the charge. During the stimulation state and the active recharge state, blanking circuitry 446 may block the sensing signal. For example, first switches 449, 451 may be configured to switch-out calibration capacitors 452, 453, respectively, when stimulation generation circuitry 204 provides stimulation and when stimulation generation circuitry 204 provides active recovery.

Subsequent to entering the active recharge state, stimulation generation circuitry 204 may be configured to enter a passive recharge state on the control electrodes. Active recharge states may use a relatively large power expenditure from power source 214 of IMD 200 to generate the opposing current. In order to conserve power for extending the life of IMD 200, at least a portion of the active recharge state in stimulation generation circuitry 204 may be replaced by a passive recharge state. While in the passive recharge state, in this example, switching elements 449, 451 may be configured to switch-in calibration capacitors 452, 453, respectively, when stimulation generation circuitry 204 does not provide stimulation and during a signal acquisition state. Resistors 448, 450 may help to limit an amount of electrical current of circuit 400.

While operating in the passive recharge state, processing circuitry 208 may auto-zero outputs to amplifier circuitry 456. Auto-zeroing the outputs to may calibrate the sensing circuitry 206 for detecting sensing signals from patient tissue. To auto-zero the outputs, processing circuitry 208 may close calibration switches 460, 461 of auto-zero circuitry 454 to connect the outputs to ground. Offsets may be stored on calibration capacitors 452, 453 during passive recharge may be used to provide common mode rejection seen at the input of amplifier circuitry during a signal acquisition state, which may improve the accuracy of a sensing signal (e.g., an ECAP signal) generated during the signal acquisition state.

Processing circuitry 208 of IMD 200 may cause stimulation generation circuitry 204 to deliver, on governing electrodes, a governed therapy to the patient after sensing for the evoked compound action potential signal. For example, processing circuitry 208 may be configured to cause sensing circuitry 206 to sense, during the passive recharge state, for a sensing signal (e.g., an ECAP signal). Following sensing for the sensing signal, processing circuitry 208 may cause stimulation generation circuitry 204 to deliver a governed therapy to the patient tissue on the governing electrodes based on the sensing signal.

Figure 5:
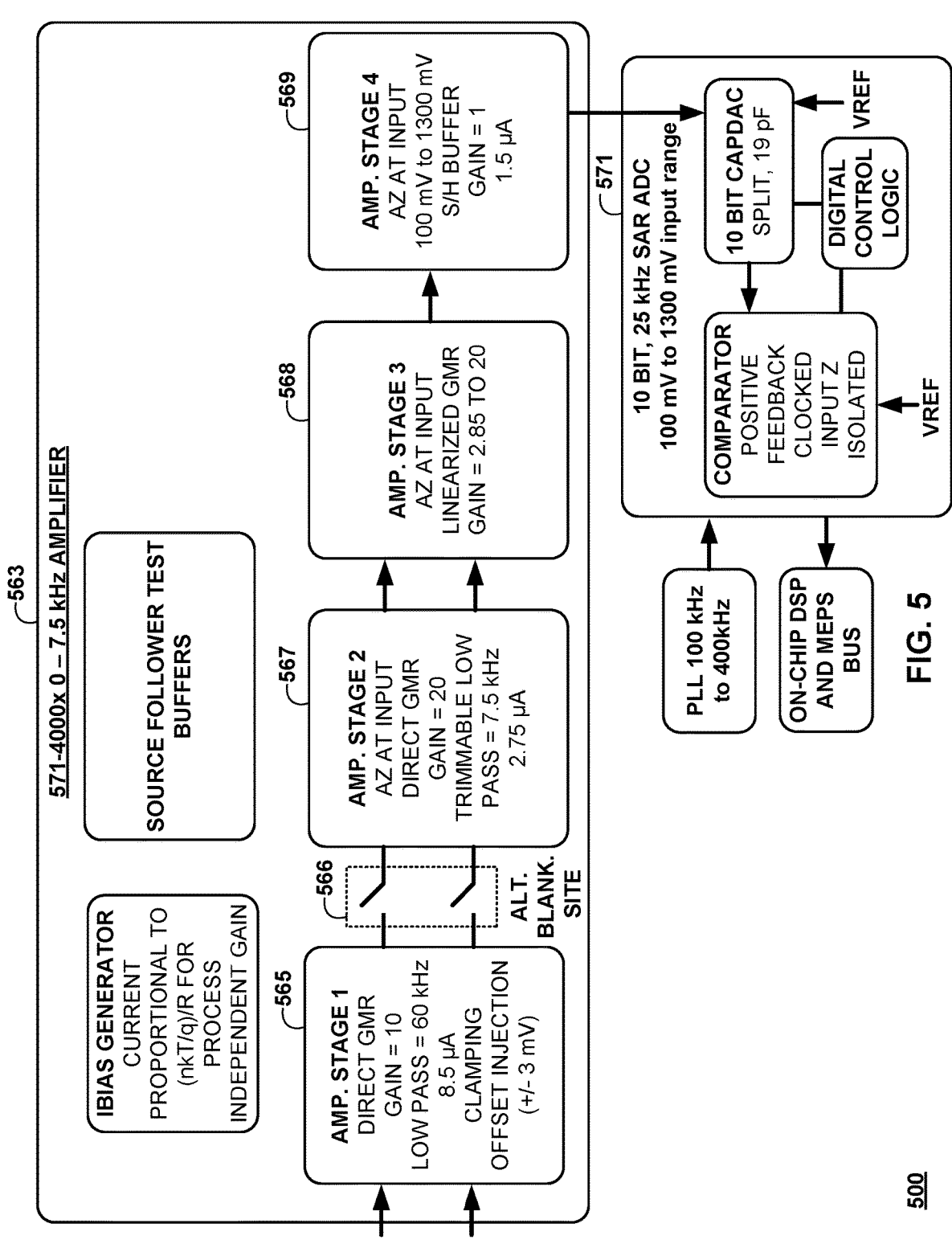
FIG. 5 is a conceptual diagram illustrating an example digital circuit for determining a sensor signal, in accordance with one or more techniques of this disclosure.

FIG. 5 is a conceptual diagram illustrating an example digital circuit 500 for determining a sensor signal, in accordance with one or more techniques of this disclosure. In this example, first amplifier stage 565 of amplifier circuitry 563 may pre-amplify a sensing signal output by analog circuitry (e.g., analog circuitry 400 of FIG. 4).

As shown, first amplifier stage 565 may include a transconductance amplifier (referred to herein as a "GMR amplifier"), which is discussed in further detail in FIG. 14. As used herein, GMR may refer to transconductance (gm) times resistance (R). The transconductance (gm) may refer to the transconductance of the input stage which converts a differential voltage into a differential current (e.g., gm=Iout/Vin.) Iout is then passed a resistance "R", resulting in Vout=R*Iout. Vout/Vin of the 2 steps=gm*R. These circuits are thus referred to herein as "GMR" circuits.

First amplifier stage 565 may comprise a direct GMR stage with gain of 10, a low pass filter of 60 kHz, a current consumed of 8.5 μA, apply clamping of internal nodes for rapid recovery of out of range conditions, and an offset injection of +/−30 mV (+/−3 mV input referred) at the stage output. Circuit 500 may include alternative blanking timing circuitry 566, which may provide a blanking function. For example, alternative blanking timing circuitry 566 may switch-out second amplifier stage 567 during a stimulation state and/or an active recovery state. In this example, alternative blanking timing circuitry 566 may switch-in second amplifier stage 567 during a passive recharge state. Alternative blanking timing circuitry 566 may switch-out second amplifier stage 567 during a governed therapy state.

Second amplifier stage 567 may be configured to auto-zero at input and may include a direct GMR with gain of 20. A direct GMR stage may become non-linear when the input exceeds a threshold voltage range, for example, approximately +/−20 mV. Second amplifier stage 567 may include a trimmable low pass filter of 7.5 kHz. Second amplifier stage 567 may be configured to add a trimmable amount of capacitance at the output of this stage to change the pole from, for example, 60 kHz to 7.5 kHz. The gain of second amplifier stage 567 may be 20, compared to the gain of 10 of first amplifier stage 565. The power usage of second amplifier stage 567 may be less than the power usage of first amplifier stage 565 because first amplifier stage 565 amplifies noise by a factor of 10. Noise power is inversely proportional to current in these stages. Second amplifier stage 567 may include a current of 2.75 μA.

Third amplifier stage 568 may be configured to auto-zero at input, may comprise a linearized GMR with gain of 2.85 to 20. A linearized GMR stage may apply an interior loop feedback technique to have a linear transfer function for larger input signals.

Fourth amplifier stage 569 may be configured to auto-zero at input, with an output voltage of 100 mV to 1300 mV, may comprise S/H buffer with gain of 1, and a current of 1.5 μA. The output of fourth amplifier stage 569 may be digitized by SAR ADC 571. Fourth amplifier stage 569 may convert a high impedance input signal to a low impedance output signal. For example, fourth amplifier stage 569 may rapidly load a 19 pF sample and hold capacitor from ground, with the signal voltage to sub-mV accuracy, within about 5 μs. For instance, fourth amplifier stage 569 may comprise cascading source follower unity gain buffers.

Figure 6:
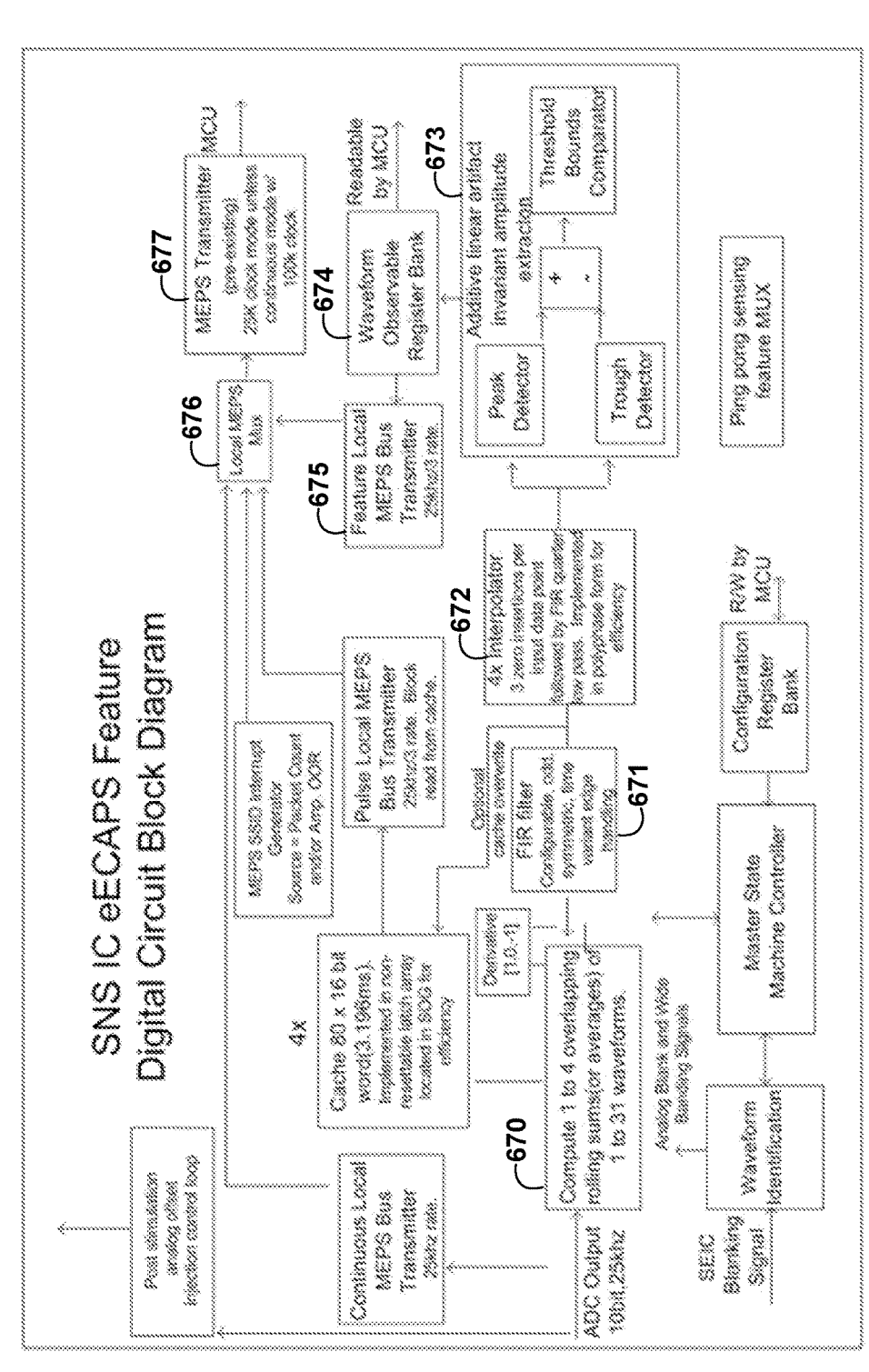
FIG. 6 is a conceptual diagram illustrating an example digital circuit for determining a sensor signal, in accordance with one or more techniques of this disclosure.

FIG. 6 is a conceptual diagram illustrating an example digital circuit 600 for determining a sensor signal, in accordance with one or more techniques of this disclosure. In the example of FIG. 6, circuit 600 may compute multiple (e.g., 1 to 4) overlapping rolling sums (or averages) of waveforms (e.g., 1 to 31 waveforms) (670), which may reduce noise. Circuit 600 may then apply a finite impulse response (FIR) filter that is, for example, configurable, odd, symmetric, time variant edge handling (671), which may further reduce noise. Circuit 600 may perform a derivative on the output of step 670 to make an artifact invariant to a presence of an additive linear artifact (see step 1904 of FIG. 19). Circuit 600 may select the average directly from step 670 or the derivative on the average as the input to the FIR filter.

In this example, circuit 600 may apply an interpolator (e.g., a 4× interpolator) using zero insertions (e.g., 3 zero insertions) per input data point that may be followed by a FIR quarter low pass and that is implemented in, for example, polyphase form for efficiency (672). Circuit 600 may perform additive linear artifact invariant amplitude extraction, which is described in further details with respect to step 1908 of FIG. 19 (673) and generate a waveform observable register bank (674). In this example, circuit 600 may output a representation of waveform a Medtronic Extensible Programmable Sensor Bus (MEPS) bus transmitter to a master control unit (MCU) (675) using a local MEPS multiplexer (676). While the above example uses a MEPS, some examples may use another bus. Circuit 600 may output the representation of the waveform using a MEPS transmitter (e.g., 25 kHz clock mode unless continuous mode w/100 kHz clock) (677).

Figure 7:
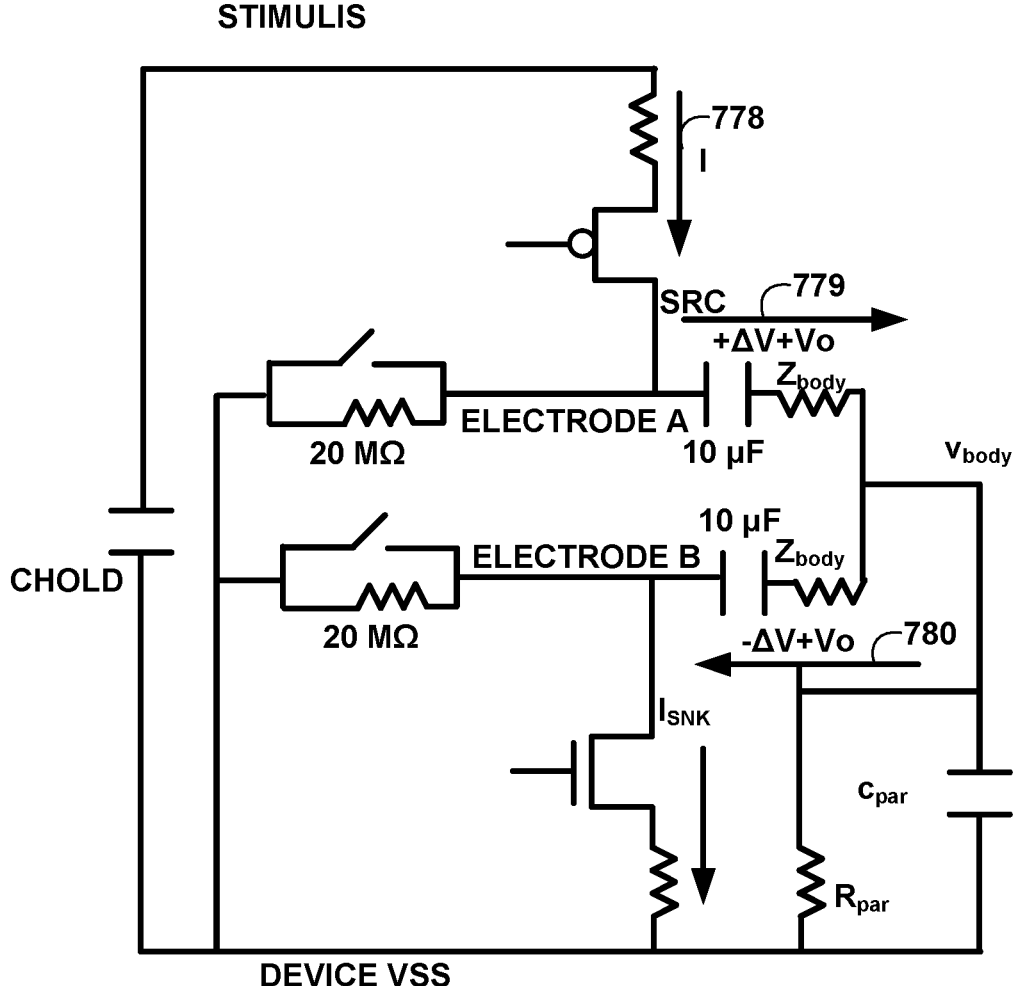
FIG. 7 is a circuit diagram illustrating an example stimulus state of operation, in accordance with one or more techniques of this disclosure.

FIG. 7 is a circuit diagram illustrating an example stimulus state of operation, in accordance with one or more techniques of this disclosure. The stimulus hardware of FIG. 7 is an example of an electronically evoked compound action potential (ECAP) stimulus hardware. This stimulus hardware may be used to establish the relative voltage between device ground and the common body voltage, which may be important to ECAP sensing. In the example of FIG. 7, stimulation generation circuitry 204 may apply current 778 to perform a stimulation state operation, which results in a voltage (e.g., $+\Delta V+Vo$) being applied to patient 102 (779), which results in a total charge Q (780). The total charge Q may result in a residual voltage left on the 10 µF AC coupling capacitors of $+\Delta V+Vo$ and $-\Delta V+Vo$, where Vo is the initial condition on the capacitor.

In FIG. 7, $Z_{body}$ represents the electrode body interface. The electrode body interface may be described as an ion double layer capacitor in parallel with an ion oxidation reduction pathway, which may be described by the Butler-Volmer equation. The ion double layer capacitor in parallel with the ion oxidation reduction pathway may be in series with an Ohmic body impedance. A further simplified model of the electrode body interface may be referred to as Randles circuit, which is a leaky capacitor in series with an ohmic body impedance.

Figure 8:
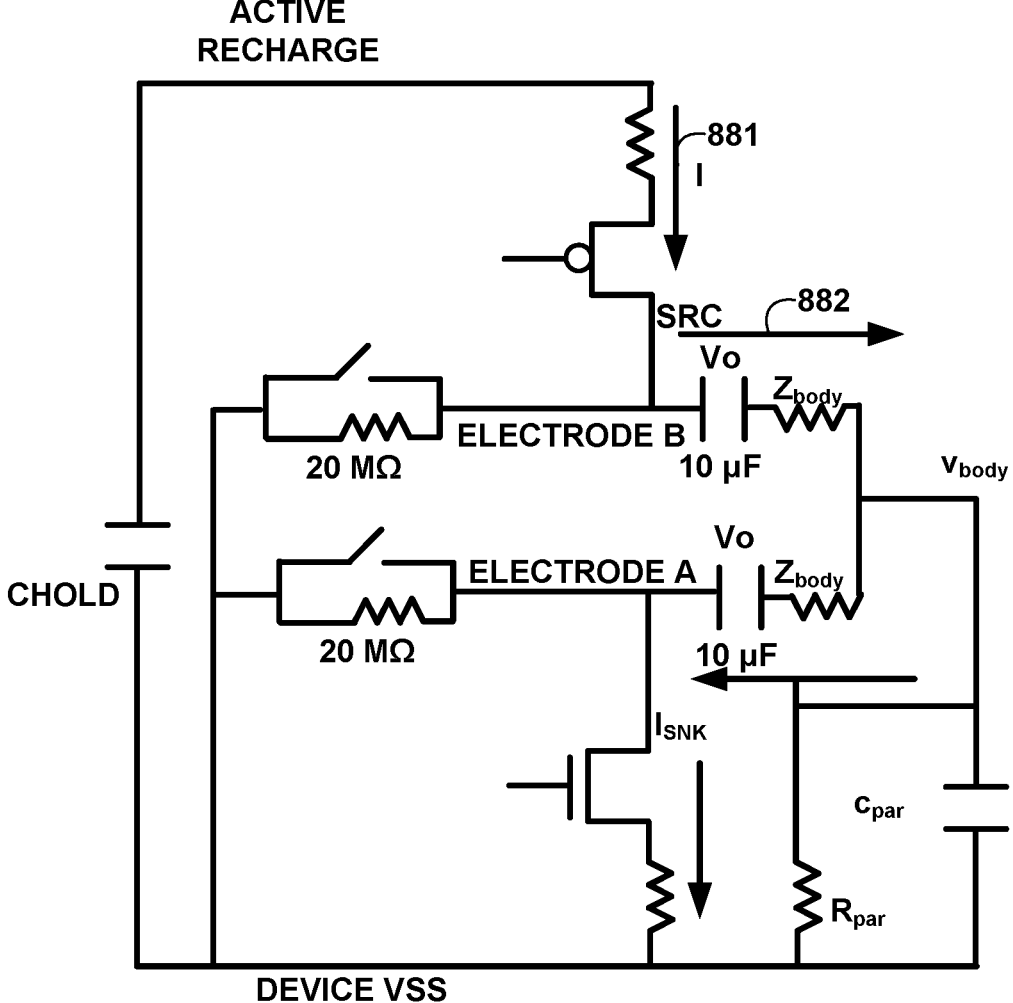
FIG. 8 is a circuit diagram illustrating an example active recharge state of operation, in accordance with one or more techniques of this disclosure.

FIG. 8 is a circuit diagram illustrating an example active recharge state of operation, in accordance with one or more techniques of this disclosure. In the example of FIG. 8, stimulation generation circuitry 204 may apply current 881 to perform an active recharge state operation (882). The current being applied to patient 102 may remove the charge on the 10 µF coupling capacitors that was added during stimulus, which may return the capacitors to the initial voltage (Vo).

Figure 9:
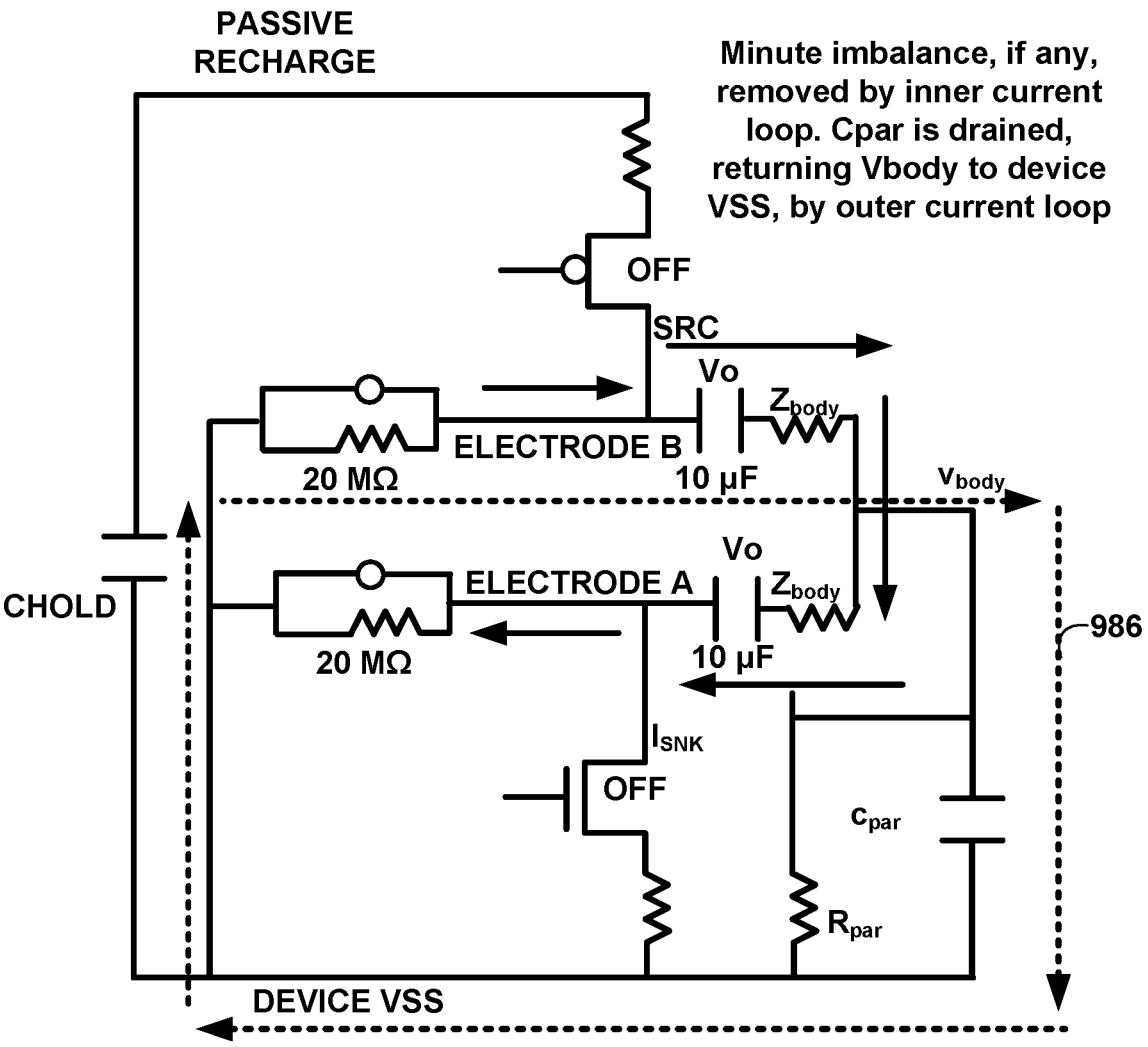
FIG. 9 is a circuit diagram illustrating an example passive recharge state of operation, in accordance with one or more techniques of this disclosure.

FIG. 9 is a circuit diagram illustrating an example passive recharge state of operation, in accordance with one or more techniques of this disclosure. Loop 986 may rapidly drain $C_{par}$ (e.g., 10 µs) to make $V_{body}$ equal device ground, which may help to improve an accuracy of a sensing state.

Figure 10:
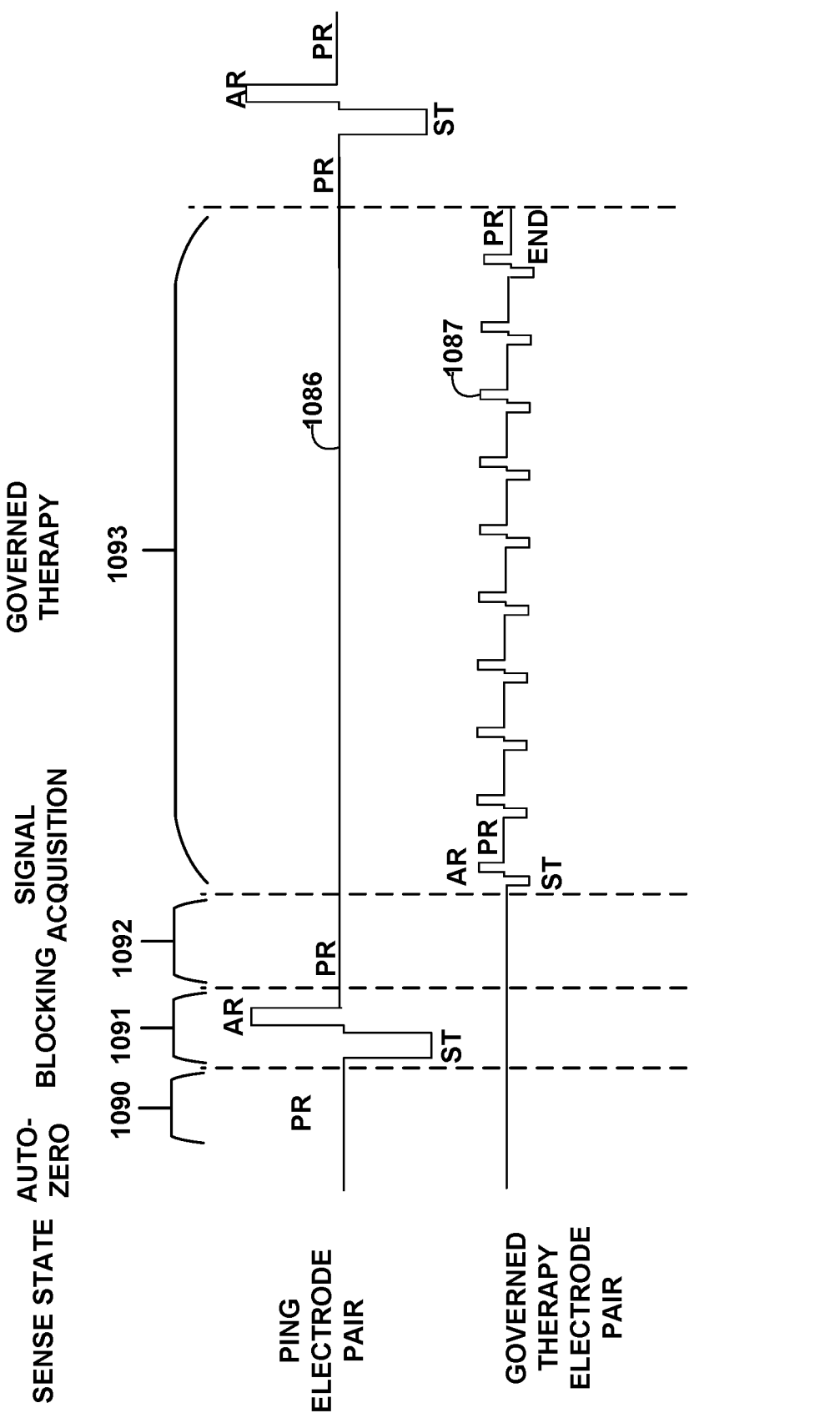
FIG. 10 is a waveform timing diagram illustrating example states of operation, in accordance with one or more techniques of this disclosure.

FIG. 10 is a waveform timing diagram illustrating example states of operation, in accordance with one or more techniques of this disclosure. In the example of FIG. 10, processing circuitry 208 may operate in 4 states of operation. The ordinate axis of FIG. 10 represents a ping electrode pair current 1086 and a governed therapy electrode pair current 187 and the abscissas axis of FIG. 10 represents time.

In the auto-zero state 1090, processing circuitry 208 may obtain a "best" approximation of the differential and common mode offset that will be seen at the input of the amplifier during signal acquisition phase 1092 so that the differential and common mode offset can be cancelled. Details of the auto-zero state 1090 are discussed with respect to FIGS. 11A, 11B. In the blocking state 1091, processing circuitry 208 may be configured to recover quickly from the presence of a ping stimulus and active recharge (e.g., about 10 V) and be able to sense a sensing signal as low as 10 $\mu V_{pp}$, as early as 200 µs after the ping stimulus, a factor of 1 million in voltage difference. Details of the blocking state 1091 are discussed with respect to FIG. 12. In the signal acquisition state 1092, processing circuitry 208 may be configured to acquire a sensing signal to measure an amplitude value (e.g., an ECAP amplitude value). Details of the signal acquisition state 1092 are discussed with respect to FIG. 13.

In governed therapy stimulus state 1093, processing circuitry 208 may perform titrated therapy based on a feature of the sensing signal (e.g., an ECAP amplitude value). For example, during governed therapy stimulus state 1093, stimulation generation circuitry 204 may deliver stimulus according to FIGS. 7-9. Passive recharge of the governed (therapy) electrodes may not be the desired device state to perform an auto-zero. Instead, system 100 may be configured to the ping electrode passive recharge state (e.g., auto-zero state 1090).

Figures 11A, 11B:
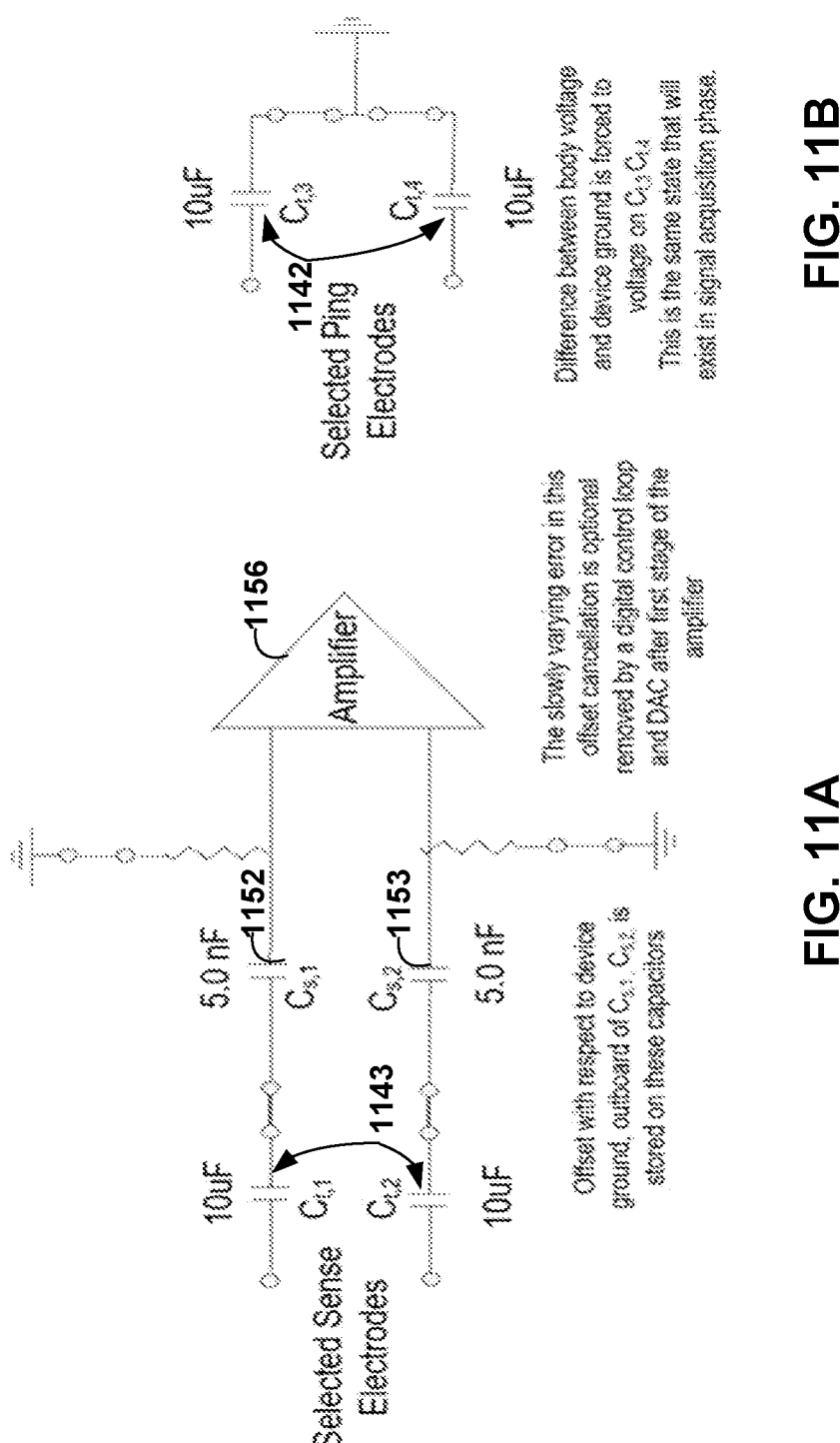
FIGS. 11A and 11B are a circuit diagrams illustrating an example of sensing circuitry during an auto-zero state of operation, in accordance with one or more techniques of this disclosure.

FIGS. 11A and 11B are a circuit diagrams illustrating an example of sensing circuitry during auto-zero state 1090 of operation, in accordance with one or more techniques of this disclosure. Cancelling differential offset may be beneficial for observing, with a high resolution, sensing signals, which may include 10 $\mu V_{pp}$ (Volts peak-to-peak) to 300 $\mu V_{pp}$ signals. Cancelling common mode offset may be beneficial to staying within the common mode input range of high performance, low voltage, amplifier components. Furthermore, small variations in the common mode input signal may produce an offset, resulting from the finite common mode rejection ratio of the amplifier. In this auto-zero state 1090 the common and differential mode offset at the sense amplifier input may be stored on the auto-zero capacitors 1152 ("Cs,1") and 1153 ("Cs,2"), which may be examples of calibration capacitors 452, 453, respectively. During measurement, auto-zero capacitors 1152, 1153 may be placed in series with amplifier 1156, which may help to cancel differential offset and/or common mode offset. During auto-zero state 1090, auto-zero capacitors 1152, 1153 may store the offset due to low frequency aggressors, such as, for example, 60 Hz noise, as close in time as possible to the signal acquisition state, which may maximize the cancellation of differential offset and/or common mode offset. In some examples, during auto-zero state 1090, auto-zero capacitors 1152, 1153 may store an inherent offset the device is expected to see in the subsequent signal acquisition state. Storing the inherent offset may be accomplished by placing the device (e.g., IMD 110) in the same configuration that will exist in the signal acquisition state, when performing the auto-zero operation of auto-zero state 1090.

FIG. 11B represents a passive recharge of the ping electrodes. In the configuration of FIG. 11B, two charge balanced capacitors 1142 ("$C_{t,3}$" and "$C_{t,4}$"), which may be examples of AC coupling capacitors 442 of FIG. 4 are connected between device ground and human tissue through the ping electrodes. AC coupling capacitors 1142 may control the voltage (see FIG. 9). The common mode voltage between device ground and the common body voltage may be the non-zero voltage stored on these capacitors.

Back to FIG. 11A, the common mode voltage seen at the input of amplifier 1156 may incorporate the common mode voltage stored on charge balanced capacitors 1142 as well as the second pair of charge balanced capacitors 1143 ("$C_{t,1}$" and "$C_{t,2}$"), which may be examples of AC coupling capacitors 442 of FIG. 4, that exist between the body and sense amplifier input. The differential voltage seen at amplifier 1156 may be the differential voltage at the sense electrode interface and on charge balanced capacitors 1143. Charge balanced capacitors 1143 may be configured to use electrodes as therapy electrodes. Charge balanced capacitors 1143 may help to protect against DC current flowing into the body of patient 102, resulting in tissue/electrode damage, during therapy. Charge balanced capacitors 1143 also protect against silicon failure in the field, resulting in DC current, that may also result in tissue damage of patient 102. As system 100 may be highly configurable for selected electrodes, the sense and ping electrodes may be selectable between 17 options, at the device level. The offset measured by this auto-zero process is only an estimate.

Figure 12:
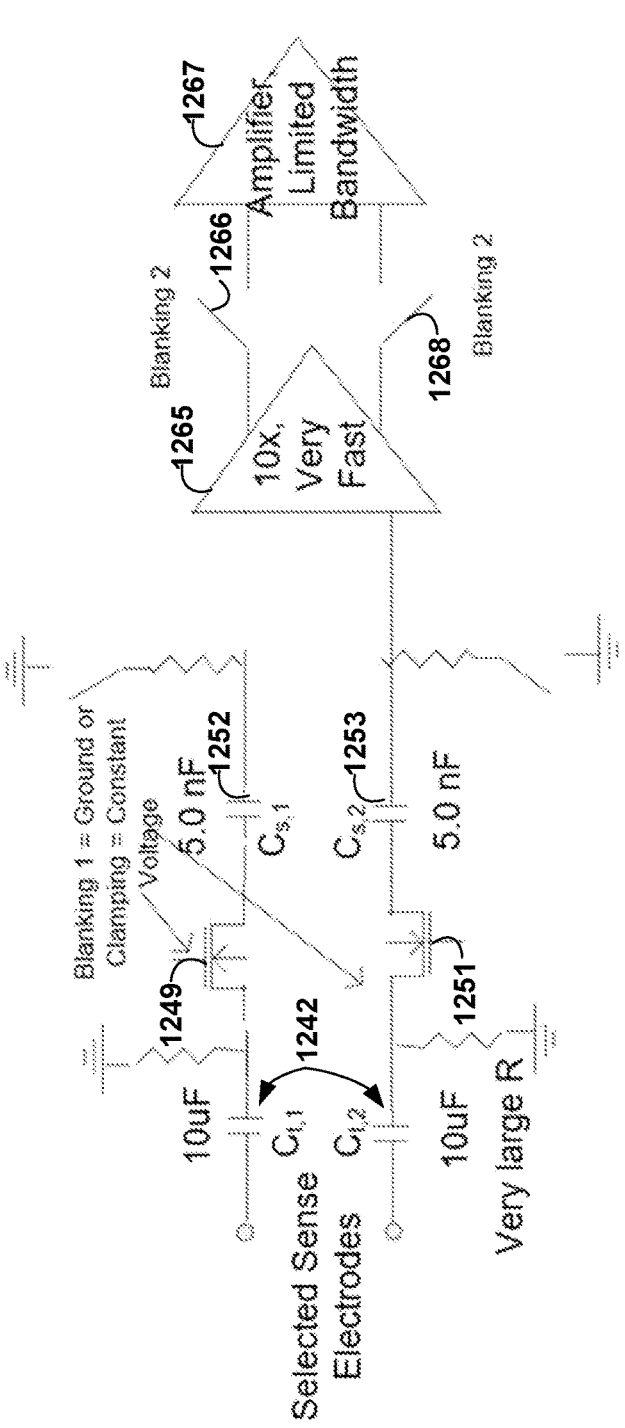
FIG. 12 is a circuit diagram illustrating an example of sensing circuitry during a blocking state of operation, in accordance with one or more techniques of this disclosure.

FIG. 12 is a circuit diagram illustrating an example of sensing circuitry 1200 during a blocking state of operation, in accordance with one or more techniques of this disclosure. FIG. 12 illustrates an example blanking operation. The blanking operation may include processing circuitry 208 opening switches 1249, 1251 to prevent capacitors 1252, 1253 ("$C_{s,1}$" and "$C_{s,2}$") from changing their voltages. Capacitors 1242 may be examples of AC coupling capacitors 442 of FIG. 4 and/or the 10 μF capacitors in FIG. 9. The blanking operation may help to stop the sensing signal from being received by second amplifier stage 1267.

Circuit 1200 may be configured to perform a blanking operation or clamping using switches 1249, 1251 and a blanking operation using blanking switches 1266, 1268. For example, processing circuitry 208 may blank, using switches 1249, 1251, the input of first amplifier stage 1265 at a time (e.g., at least 40 μs) beyond active recharge (e.g., at the end of blocking state 1091 of FIG. 10) and may blank, using blanking switches 1266, 1268, an input of second amplifier stage 1267 at a time (e.g., at least 60 μs) beyond the active recharge, which may help to allow a transient of the received sensing signal to reach steady state prior to propagating the received sensing signal to longer time constant stages downstream (e.g., second amplifier stage 1267 or second amplifier stage 1267 with one or more additional amplifier stages).

In some examples, switches 1249, 1251 may be configured to only clamp the sensing signal to a component safe voltage range. For example, processing circuitry 208 may clamp, using switches 1249, 1251, the input of first amplifier stage 1265 to a target voltage range (e.g., a component safe voltage range). In this example, processing circuitry 208 may blank, using blanking switches 1266, 1268, an input of second amplifier stage 1267 at a time (e.g., at least 60 μs) beyond the active recharge (e.g., at the end of blocking state 1091 of FIG. 10), which may help to allow a transient of the received sensing signal to reach steady state prior to propagating the received sensing signal to longer time constant stages downstream (e.g., second amplifier stage 1267 or second amplifier stage 1267 with one or more additional amplifier stages).

Figure 13:
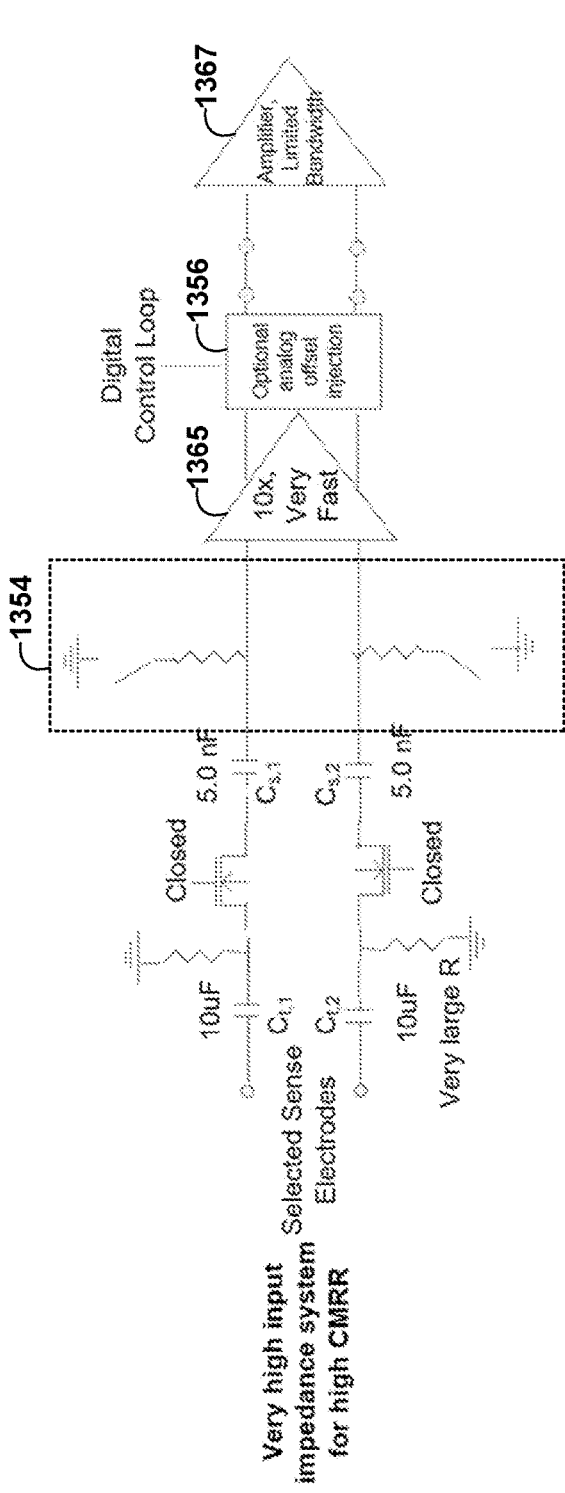
FIG. 13 is a circuit diagram illustrating an example of sensing circuitry during a signal acquisition state of operation, in accordance with one or more techniques of this disclosure.

FIG. 13 is a circuit diagram illustrating an example of sensing circuitry 1300 during a signal acquisition state of operation, in accordance with one or more techniques of this disclosure. During signal acquisition state 1092, sensing circuitry 1300 may wide band a high pass filter (e.g., disabling the high pass filter). For example, sensing circuitry 1300 may make the passband wider by moving the high pass poles from ~100 Hz to ~0 Hz. The frequency of a pole is fhp (Hz)=1/(2*pi*R*C). By opening up the switch in series with the resistor R becomes infinite and fhp (Hz)=0.

The benefit of disabling the high pass filters is more than just preserving all low frequency content of the targeted signal. Sensing circuitry 1300 may exhibit offset jitter that cannot fully be controlled by any of our offset control mechanisms. When a step offset is passed through a cascade of 4 high pass filters (instead of an auto-zeros process), the step response may result in a complicated background signal that may be hard to separate from the sensing signal (e.g., an ECAP signal), and resulting amplitude value that is desirable to extract. In contrast, it is much easier for IMD 110 to devise a measurement of amplitude extraction that is invariant to a flat background signal. For example, a peak minus trough amplitude measurement is invariant to an offset, provided the offset is within the dynamic range of the amplifier.

Sensing circuitry 1300 may help to increase the common mode rejection ratio (CMRR) of the amplifier system during signal acquisition state 1092, which may help to avoid signal degradation by common mode aggressors in the body of patient 102. The disconnection of resistors of grounding circuitry 1354 at the amplifier input may help to force the input impedance extremely high, corresponding primarily to the capacitance of the differential pair at the input of the amplifier. The input impedance at the body, which ranges from 30 kΩ at low frequencies to 1 kΩ at higher frequencies, and do not match, form an impedance divider with the amplifier input impedance, which may degrade the CMRR. If the resistors of ground circuitry 1354 were not switched out, the common mode rejection ratio of the system may be poor, and sensing signals may not be measurable. During signal acquisition state 1092, the second differential offset cancelling mechanism, using a digital control loop, may be applied.

In accordance with the techniques of the disclosure, injection circuitry 1356 may be configured to provide a differential offset cancelling mechanism. The differential offset cancelling mechanism of injection circuitry 1356 may help to account for a slowly varying change in the offset between the auto-zero state (e.g., at the end of auto-zero state 1090) and after a ping pulse (e.g., at the end of blocking state 1091). For example, the offset difference between the auto-zero state and after the ping pulse may slowly vary as patient 102 changes a posture state (e.g, from supine to standing). In this example, injection circuitry 1356 may be configured to inject a differential offset that cancels out changes in body interface since the auto-zero state 1090.

Injection circuitry 1356 may be configured to inject a cancelling offset between the first stage amplifier 1365 and second stage of amplifier 1367. Injecting the cancelling offset between first stage amplifier 1365 and second stage of amplifier 1367 may represent an improved operation compared to systems that inject the slowly varying cancelling offset before first stage amplifier 1365 or after second stage of amplifier 1367. For example, when injection circuitry 1356 injects the cancelling offset between first stage amplifier 1365 and second stage of amplifier 1367, fidelity requirements may be relaxed compared to systems that inject the slowly varying cancelling offset before first stage amplifier 1365 by, for example, having a partially amplified signal from first stage amplifier 1365. Moreover, when injection circuitry 1356 injects the cancelling offset after second stage amplifier 1367, the allowed range of the amplifier stage 1367 may be exceeded.

Injection circuitry 1356 may be configured to generate the cancelling offset with a digital control loop. The digital control loop of FIG. 13 may be designed to realize a discrete time, single pole, high pass filter, with configurable pole location in the forward signal flow pathway. For example, injection circuitry 1356 may be configured to generate the cancelling offset based on a set of waveforms (e.g., digital historical waveforms). For example, injection circuitry 1356 may be configured to generate the cancelling offset based on a set of waveforms received by SAR ADC 571 of FIG. 5.

Processing circuitry 208 may be configured to determine the weighted set of digital historical offsets of waveforms based on one or more previous sensing signals that occur before the sensing signal. For example, processing circuitry 208 may generate, for each waveform of a set of previous digital waveforms, a respective weighted digital historical offset to generate a set of weighted set of digital historical offsets of waveforms. Each of the respective weighted digital historical offset may be associated with a different previous "ping pulse cycle." A ping pulse cycle may refer to a cycle of states 1090-1093 of FIG. 10, where a waveform is sensed during signal acquisition state 1092 using autozeroing techniques described herein during auto-zero state 1090.

For example, for a set of 3 previous ping pulse cycles, processing circuitry 208 may generate, for a first digital waveform associated with a first previous ping pulse cycle that occurs before a current ping pulse cycle, a first weighted digital historical offset by multiplying an offset of the first digital waveform by a first weight. In this example, processing circuitry 208 may generate, for a second digital waveform associated with a second previous ping pulse cycle that occurs before the first previous ping pulse cycle, a second weighted digital historical offset by multiplying an offset of the second digital waveform by a second weight. The second weight may be less than the first weight. In this example, processing circuitry 208 may generate, for a third digital waveform associated with a third previous ping pulse cycle that occurs before the second previous ping pulse cycle, a third weighted digital historical offset by multiplying an offset of the third digital waveform by a third weight. The third weight may be less than the second weight. While the above example uses 3 historical offsets, other examples may use 1 historical offset, 2 historical offsets, or more than 3 historical offsets (e.g., 10 historical offsets).

Injection circuitry 1356 may be configured to generate the cancelling offset by applying a closed-loop control feedback using the weighted set of digital historical offsets of waveforms. For example, injection circuitry 1356 may apply an integral controller (e.g., I controller) to the weighted set of digital historical offsets of waveforms to generate the cancelling offset.

FIG. 14 is a circuit diagram illustrating an example GMR amplifier 1400, in accordance with one or more techniques of this disclosure. GMR amplifier 1400 may be an example of first amplifier stage 565 of FIG. 5. GMR amplifier 1400 may exhibit the following characteristics:

1) Low noise amplification with minimal power.
2) Balanced and high input impedance for optimal system level CMRR.
3) Very high common mode and power supply rejection ratio.
4) Very fast response to recover from post-blocking state transients.
5) Controlled gain over temperature and process variation.

To achieve these goals, the design of FIG. 14 does not use the more common bio-amplifier, low noise amplifier (LNA) approaches which utilize feedback. A common form of this is the capacitive feedback network (CFN). This is because CFN may cost significant extra power and may be slower with post-blocking state transient recovery. Instead, GMR amplifier 1400 may use feedback's sister approach of invariance, where process parameters and temperature are made to drop out of the forward transfer function by having terms in the numerator and denominator cancel, by design, without feedback. This approach is targeted to the objectives above for the first gain stage. After the first stage, implementation approach is less important as the power required drops with gain squared for a targeted signal to noise amplitude ratio. Gain squared in this case may be 100. The invariant GMR approach (gm (transconductance)*r (resistance)) may be highly suited to the of the first stage amplifier. The gain achievable by this circuit is limited, but this limitation works well with the analog offset injection control loop that requires offset be injected in a middle stage of amplification to avoid noise and fidelity sensitivities to injection, avoid limitations in the dynamic range of the system, and isolate this circuitry from degrading the 5 goals stated above for the input state.

Through the analysis below, the gain may be well controlled and be at least partially invariant to process variation and temperature. In fact, the gain is controlled by the ratio of two resistors which share the same process variation and is proportional the scaling of the $I_{BIAS}$ current sent to the amplifier. Signal to noise amplitude is observed to be proportional to the square root of the bias current sent to the different pair. By properly selecting the resistor ratio and current, required noise and gain can be independently targeted. Thus, GMR amplifier 1400 may have no feedback in the forward signal path, which would have resulted in a slower and higher current system, yet may be controlled through the invariance technique. Also, the input impedance of GMR amplifier 1400 may be matched and very high.

$$\text{gain} = g_m R_{out}$$

$$\text{but}$$

$$g_m = \frac{1}{2} * \frac{q}{nkT} * M_1 * I_{bias} \quad \text{in weak inversion}$$

$$I_{bias} = \ln(2) * \frac{nkT}{q} * \frac{1}{R_{bias}} \quad \text{in weak inversion}$$

$$\text{so}$$

$$\text{gain} = \frac{M_1 * \ln(2)}{2} \frac{R_{out}}{R_{bias}}$$

where $M_1$ is a fraction of a bias gain (e.g., $I_{BIAS}$*M), $R_{out}$ is resistor 1409, and $R_{bias}$ is resistor 1407.

Figures 15A, 15B:
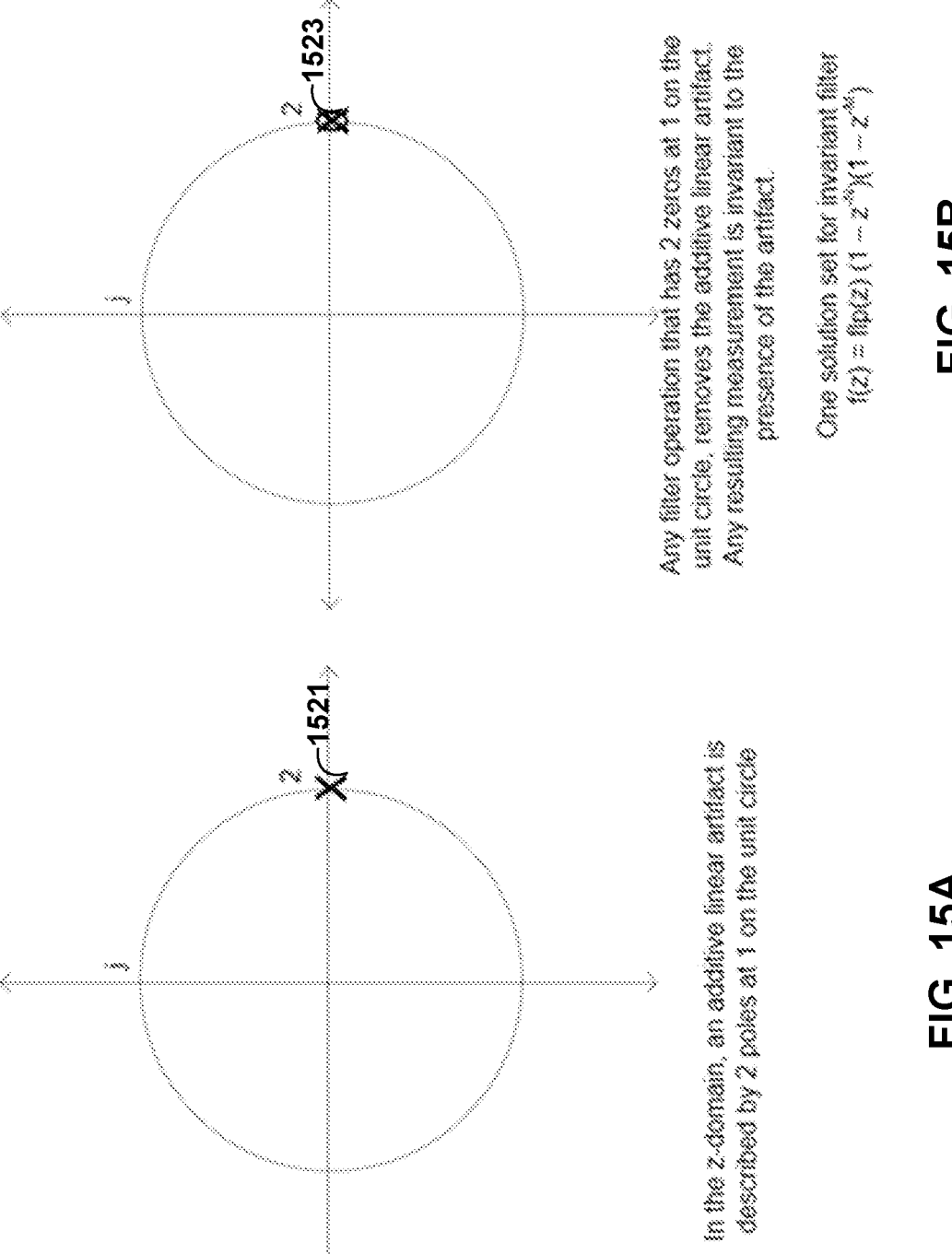
FIGS. 15A and 15B are pole-zero plane plots illustrating an example of an extraction of a sensing signal from a digitized waveform, in accordance with one or more techniques of this disclosure.

FIGS. 15A and 15B are pole-zero plane plots illustrating an example of an extraction of a sensing signal from a digitized waveform, in accordance with one or more techniques of this disclosure. In FIG. 15A, an additive linear artifact is described by 2 poles 1521 at 1 on the unit circle, which may represent a linear line (see FIG. 16). In FIG. 15B, any filter operation that has two zeroes 1523 at one on the unit circle, removes the additive linear artifact of FIG. 15A. Any resulting measurement may be invariant to the presence of the artifact. An example solution for the invariant filter may include f(Z)=flp(z)(1−z$^{-n}$)(1−z$^{-m}$), where 'n'=2 corresponds to a derivative (e.g., step 1904) and 'm' corresponds to a much larger number equal to the separation between peak and trough, of the derivative signal, in time steps, which may be implemented in step 673 of FIG. 6.

Two example principles of extracting the ECAP amplitude value may include decreasing noise and aggressor content and making the measurement invariant to the presence of a time varying tissue intrinsic artifact. Noise and aggressor reduction may be achieved by: limiting the bandwidth with a digital low pass filter as thermal noise power (e.g., the dominant noise source) may be proportional to bandwidth and averaging waveforms as uncorrelated noise power decreases as 1/N, where N is the number of waveforms averaged. The artifact at the body interface may be described as an offset+line+decaying exponential. In a small enough region of measurement, this is well approximated by a line with an offset. This artifact can vary with body position, time, and other factors. To have the measurement be invariant (e.g., not change with the artifact) the measurement may be invariant to the presence of an additive linear artifact.

Figure 16:
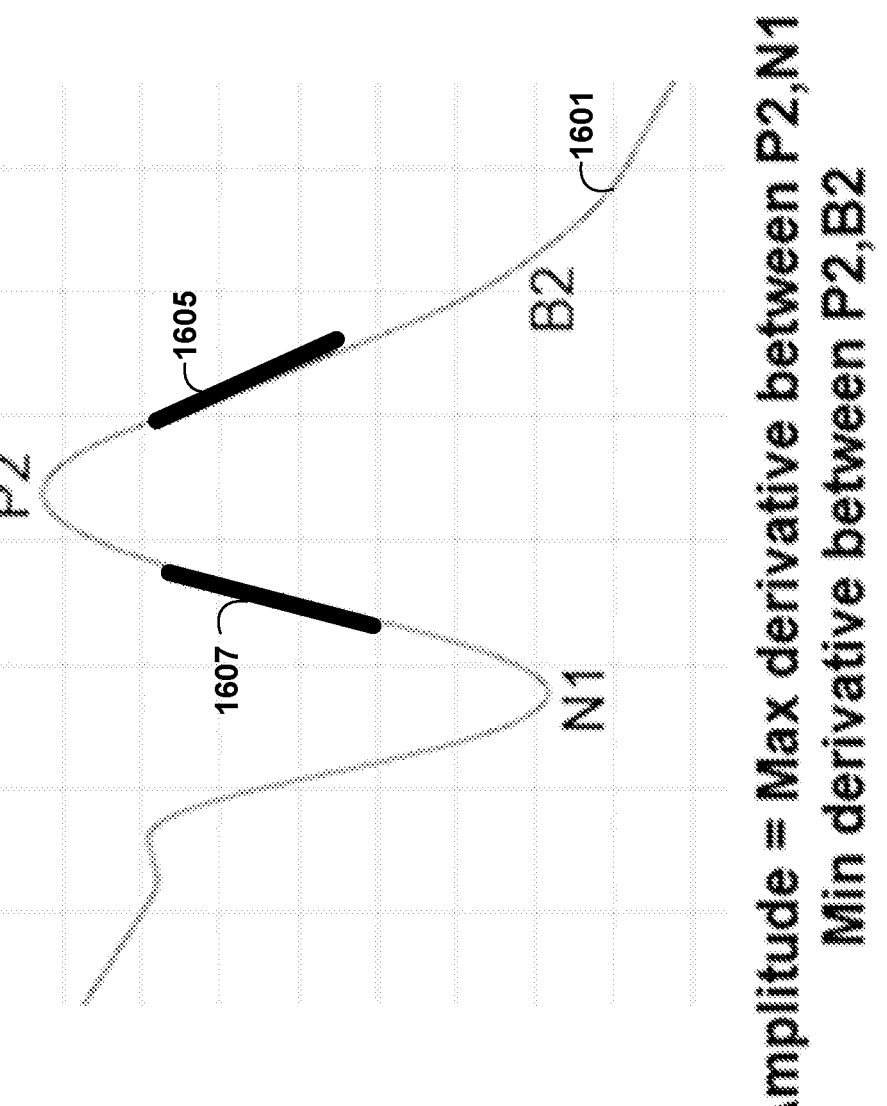
FIG. 16 is a plot illustrating an example sensing signal, in accordance with one or more techniques of this disclosure.

FIG. 16 is a plot illustrating an example sensing signal 1601, in accordance with one or more techniques of this disclosure. In the example of FIG. 16, processing circuitry 208 may calculate an amplitude value of a sensing signal (e.g., ECAP signal) as max derivative 1607 between peak P2 and trough N1 and min derivative 1605 between peak P2 and trough B2.

The nature of the low pass in the low passed derivative filter, preceding the peak−minus trough measurement, may be optimized for noise and artifact rejection, and signal strength based on a very large human database. The hardware implementation of a [1, 0, −1] filter in cascade with an 11 tap symmetric FIR filter, may yield a general form 13 tap anti-symmetric filter, with the anti-symmetry implying 1 zero at 1 on the unit circle. This general form may be configured to realize the optimal filter determined from the human database, an optimized low passed derivative filter, where the low pass allows about 4.5 kHz of content, in series with a discrete time derivative. The other zero at 1 on the unit circle of the measurement technique, for invariance to an additive linear artifact, may be achieved by a peak minus trough operation.

FIG. 17 is a flowchart illustrating an example operation for calibrating sensing circuitry of IMB 110, in accordance with one or more techniques of this disclosure. FIG. 17 is discussed with FIGS. 1-16 for example purposes only. Processing circuitry 208 may cause, when stimulation generation circuitry 204 does not provide electrical stimulation, storage of a first voltage at a first terminal 458 at first calibration capacitor 452 and storage of a second voltage at second terminal 459 at second calibration capacitor 453 (1702).

After the first voltage is stored at the first calibration capacitor 452 and the second voltage is stored at the second calibration capacitor 453 and when the stimulation generation circuitry 204 provides the electrical stimulation, processing circuitry 208 may switch out (e.g., open a switch or refrain from generating a channel in a switching element)

first calibration switch 460 to prevent the first voltage stored at first calibration capacitor 452 from changing and switch out second calibration switch 461 to prevent the second voltage stored at second calibration capacitor 453 from changing (1704). For example, processing circuitry may open calibration switches 460, 461 during stimulation (e.g., blocking state 1091 of FIG. 10), which may help to eliminate any path for a charge change on calibration capacitors 452, 453. As discussed further in FIG. 18, first switches 449, 451 may block or clamp the stimulation signal (e.g., ~10 V) from being received at inputs of amplifier circuitry 456 (e.g., first stage amplifier 565 of FIG. 5). First switches 449, 451 may be switched off during stimulation (e.g., blocking state 1091 of FIG. 10), which may also help to prevent a change in voltage stored at calibration capacitors 452, 453.

After the electrical stimulation is blocked and when stimulation generation circuitry 204 does not provide the electrical stimulation, processing circuitry 208 may determine, with sensing circuitry 206, a sensing signal based on the first voltage at first terminal 458 offset by a first calibration voltage stored by first calibration capacitor 452 and based on second voltage at second terminal 459 offset by a second calibration voltage stored by the second calibration capacitor 453 (1706). Processing circuitry 208 may cause stimulation generation circuitry 204 to deliver therapy to patient 102 based on the sensing signal (1708).

Figure 18:
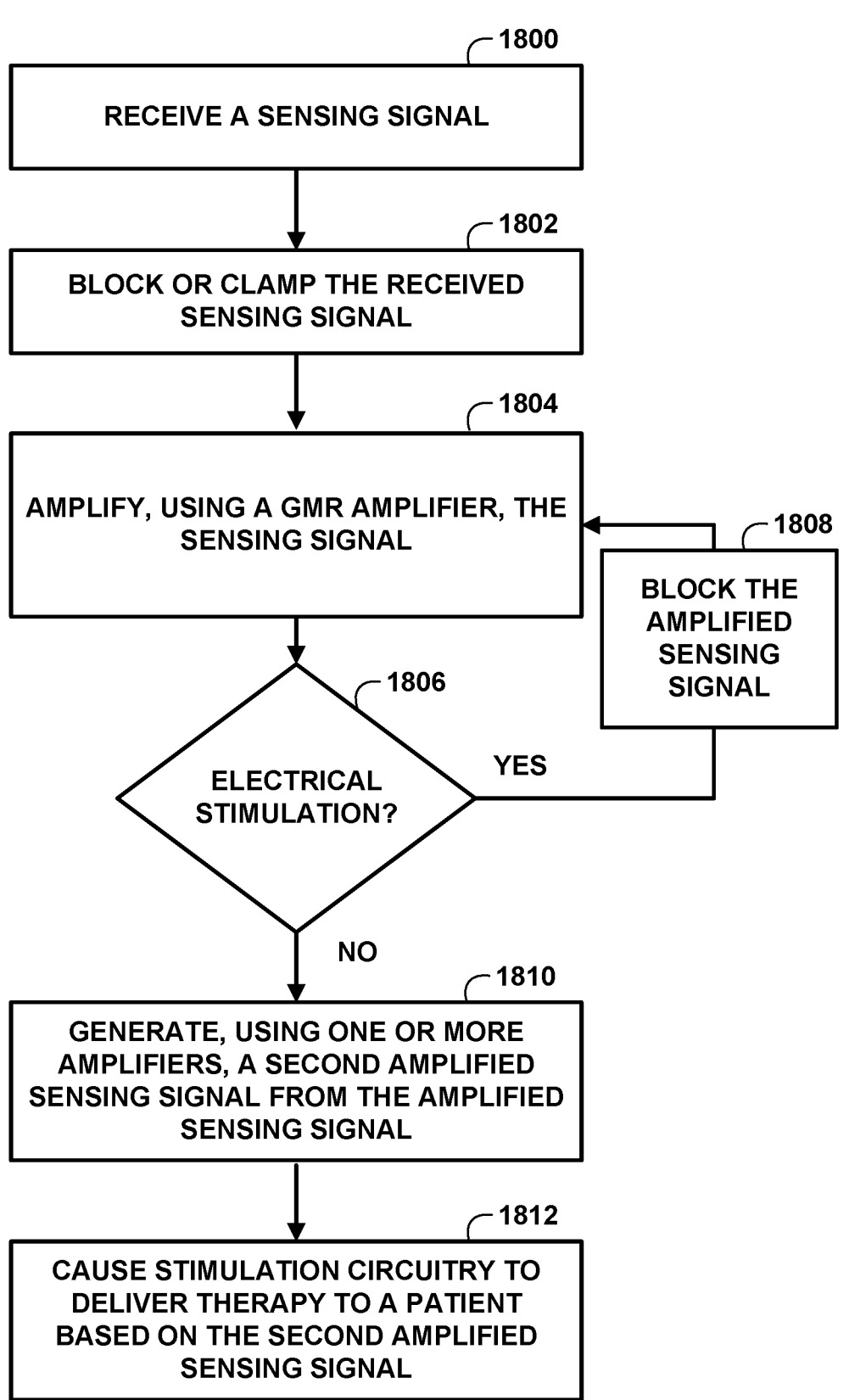
FIG. 18 is a flowchart illustrating an example operation for amplifier circuitry, in accordance with one or more techniques of this disclosure.

FIG. 18 is a flowchart illustrating an example operation for amplifier circuitry, in accordance with one or more techniques of this disclosure. FIG. 18 is discussed with FIGS. 1-17 for example purposes only. Switches 1249, 1251 may receive a sensing signal (1800). Switches 1249, 1251 may block or clamp the received sensing signal from being received by first amplifier stage 1265 (1802). For example, switches 1249, 1251 may block the received sensing signal from being received by first amplifier stage 1265 during the blocking state 1091. In some examples, switches 1249, 1251 may clamp the received sensing signal to be less than a component safe voltage range (e.g., during states 1090-1093).

First amplifier stage 1265 may amplify, for example, using a GMR amplifier, the sensing signal (1804). When stimulation generation circuitry 204 provides electrical stimulation ("YES" of step 1806), blanking switches 1266, 1268 may block the amplified sensing signal from being received by second amplifier stage 1267 (1808). For example, blanking switches 1266, 1268 may block the amplified sensing signal from being received by second amplifier stage 1267 while first switches elements 1249, 1251 clamp the sensing signal to a threshold voltage range, such as, for example, a component safe voltage range.

In some examples, switches 1249, 1251 may blank the input of first amplifier stage 1265 at a time (e.g., at least 40 μs) beyond active recharge (e.g., at the end of blocking state 1091 of FIG. 10) and blanking switches 1266, 1268 may blank an input of second amplifier stage 1267 at a time (e.g., at least 60 μs) beyond the active recharge. For example, switches 1249, 1251 may be configured to block the sensing signal after a first time delay from when stimulation generation circuitry 204 no longer provide the electrical stimulation. In this example, blanking switches 1266, 1268 may be configured to block the sensing signal after a second time delay from when stimulation generation circuitry 204 no longer provide the electrical stimulation, where the second time delay is different from the first time delay. The second time delay may be longer than the first time delay.

When stimulation generation circuitry 204 does not provide electrical stimulation ("NO" of step 1806), at least second amplifier stage 567 may generate, using one or more amplifiers, a second amplified sensing signal from the amplified sensing signal (1810). Processing circuitry 208 may cause stimulation generation circuitry 204 to deliver therapy to patient 102 based on the second amplified sensing signal (1812).

FIG. 19 is a flowchart illustrating an example operation for feature extraction, in accordance with one or more techniques of this disclosure. FIG. 19 is discussed with FIGS. 1-18 for example purposes only. Processing circuitry 208 may generate a waveform based on a sensing signal. For example, processing circuitry 208 may determine an averaged waveform from an amplified sensing signal (1902). Processing circuitry 208 may perform a derivative operation on the averaged waveform, which supplies one zero at 1 on the unit circle (1904).

Processing circuitry 208 may FIR filter, after performing the derivative operation, the averaged waveform to generate a FIR filtered waveform, thereby decreasing noise bandwidth (1906). The FIR filter may primarily apply low-pass filtering. Processing circuitry 208 may apply a peak minus trough operation to the FIR filtered waveform to measure an amplitude value (e.g., an ECAP amplitude value) of the FIR filtered waveform, which supplies one zero at 1 on the unit circle, making the total measurement invariant to an additive linear artifact (1908). As shown in FIG. 15B, a solution set for an invariant filter may include $f(Z)=flp(z)(1-z^{-n})(1-z^{-m})$, where 'n'=2 corresponds to a derivative (e.g., step 1904) and 'm' corresponds to a much larger number equal to the separation between peak and trough, of the derivative signal, in time steps (e.g., step 1908), which together is invariant to an additive linear artifact. That is, for example, $(1-z^{-m})$ may correspond to subtracting the present value from the value m steps before (e.g., step 1908). The artifact may be from the body interface and may be described as an offset+line+ decaying exponential. Processing circuitry 208 may cause stimulation generation circuitry 204 to deliver therapy to patient 102 based on the amplitude value (1910).

Figure 20:
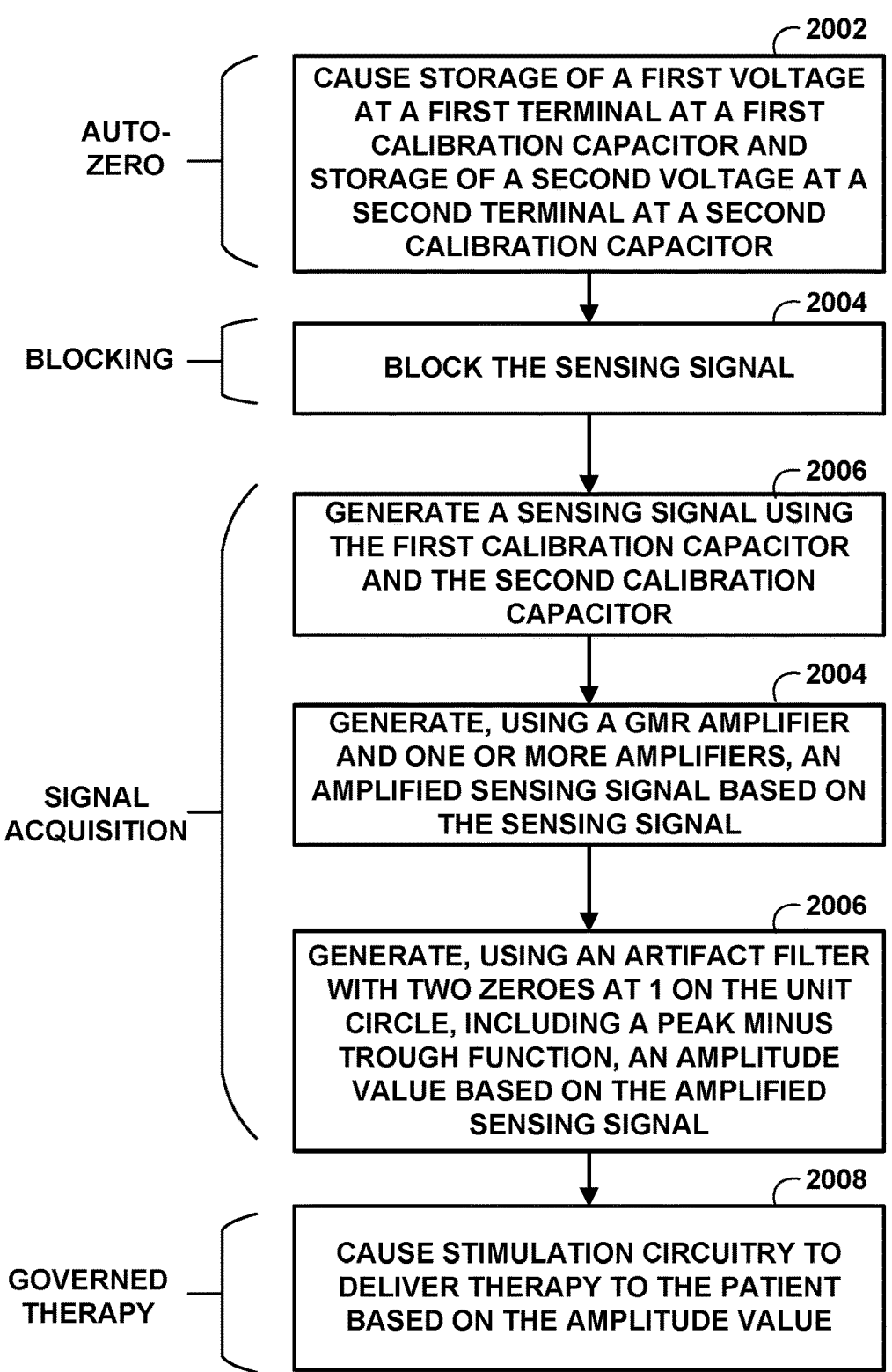
FIG. 20 is a flowchart illustrating an example operation for providing therapy based on a sensing signal, in accordance with one or more techniques of this disclosure.

FIG. 20 is a flowchart illustrating an example operation for providing therapy based on a sensing signal, in accordance with one or more techniques of this disclosure. FIG. 20 is discussed with FIGS. 1-19 for example purposes only. During an auto-zero state, processing circuitry 208 may cause storage of a first voltage at a first terminal 458 at first calibration capacitor 452 and storage of a second voltage at second terminal 459 at second calibration capacitor 453 (2002). Examples of causing storage of the first voltage and storage of a second voltage at second terminal 459 are described in FIG. 17.

During a blocking state, blanking circuitry 446 may block or clamp the sensing signal (2004). For example, when stimulation generation circuitry 204 provides electrical stimulation, blanking circuitry 446 may block or clamp the electrical stimulation from being received at amplifier circuitry 456 (e.g., an input of first amplifier stage 565 of FIG. 5). In some examples, when stimulation generation circuitry 204 provides electrical stimulation, alternative blanking timing circuitry 566 may block the amplified sensing signal from being received by second amplifier stage 567. In some examples, during the blocking state, processing circuitry 208 may switch out first calibration switch 460 to prevent the first voltage stored at first calibration capacitor 452 from changing and switch out second calibration switch 461 to prevent the second voltage stored at second calibration capacitor 453 from changing (see FIG. 17).

During a signal acquisition state, IMD 110 may generate a sensing signal using the first calibration capacitor 452 and the second calibration capacitor 453 (2006). For example, after the electrical stimulation is blocked and when stimulation generation circuitry 204 does not provide the electrical stimulation, processing circuitry 208 may generate, with sensing circuitry 206, the sensing signal based on the first voltage at first terminal 458 offset by a first calibration voltage stored by first calibration capacitor 452 and based on second voltage at second terminal 459 offset by a second calibration voltage stored by the second calibration capacitor 453.

During a signal acquisition state, IMD 110 may generate, using a GMR amplifier and one or more amplifiers, an amplified sensing signal based on the sensing signal (2004). For example, first amplifier stage 565 may amplify, using a GMR amplifier, the sensing signal to generate a first amplified sensing signal and at least second amplifier stage 567 may generate, using one or more amplifiers (e.g., amplifier stages 565-569), the amplified sensing signal from the first amplified sensing signal.

During a signal acquisition state, IMD 110 may generate, using an artifact filter with two zeroes at 1 on the unit circle, including a peak minus trough function, a feature based on the amplified sensing signal (2006). For example, processing circuitry 208 may determine an averaged waveform from the amplified sensing signal and may FIR filter the averaged waveform to generate a FIR filtered waveform, which may improve an accuracy in determining the feature. In this example, processing circuitry 208 may filter out an artifact (e.g., from the artifact at the body interface) by applying one zero at 1 on the unit circle using a derivative operation (e.g., step 1904) and apply another zero at 1 on the unit circle by applying a peak minus trough operation (e.g., step 1908; see FIGS. 15A, 15B, 16).

During a governed therapy state, processing circuitry 208 may cause stimulation generation circuitry 204 to deliver therapy to patient 102 based on the amplitude value (2008). For example, processing circuitry 208 may determine, based on the amplitude value (e.g., an ECAP amplitude value), a set of stimulation parameters, such as, for example, one or more of an electrode combination, a voltage amplitude value, or a current amplitude value, a pulse width, or a pulse frequency. The amplitude value may represent a function of how much the nerve responded to the stimulation. In this example, processing circuitry 208 may cause stimulation generation circuitry 204 to provide the stimulation with the set of stimulation parameters.

The following examples are examples systems, devices, and methods described herein.

Example 1: A system for providing therapy to a patient, the system comprising: stimulation generation circuitry configured to provide electrical stimulation to the patient; sensing circuitry configured to sense a first voltage at a first terminal and to sense a second voltage at a second terminal; and processing circuitry electrically connected to the sensing circuitry and the stimulation generation circuitry, the processing circuitry being configured to: when the stimulation generation circuitry does not provide the electrical stimulation, cause storage of the first voltage at the first terminal at a first calibration capacitor and storage of the second voltage at the second terminal at a second calibration capacitor; after the first voltage is stored at the first calibration capacitor and the second voltage is stored at the second calibration capacitor and when the stimulation generation circuitry provides the electrical stimulation, switch out a first calibration switch to prevent the first voltage stored at the first calibration capacitor from changing and switch out a second calibration switch to prevent the second voltage stored at the second calibration capacitor from changing; while the first calibration switch is switched out and the second calibration switch is switched out and when the stimulation generation circuitry does not provide the electrical stimulation, determine, with the sensing circuitry, a sensing signal based on the first voltage at the first terminal offset by a first calibration voltage stored by the first capacitor and based on the second voltage at the second terminal offset by a second calibration voltage stored by the second capacitor; and cause the stimulation generation circuitry to deliver the therapy to the patient based on the sensing signal.

Example 2: The system of example 1, further comprising amplifier circuitry configured to: receive the sensing signal; amplify, using a first stage amplifier and at least a second stage amplifier, the sensing signal to generate an amplified sensing signal; and wherein the processing circuitry is configured to cause the stimulation generation circuitry to deliver the therapy based on the amplified sensing signal.

Example 3: The system of example 2, wherein to amplify, the first stage amplifier amplifies the sensing signal to a first amplified sensing signal for output to the second stage amplifier and wherein the amplifier circuitry further comprises a set of blanking switches configured to: when the stimulation generation circuitry provides the electrical stimulation, block the first amplified sensing signal from being received at an input of the second stage amplifier; and when the stimulation generation circuitry does not provide the electrical stimulation, allow the first amplified sensing signal to be received at the input of the second stage amplifier.

Example 4: The system of example 3, further comprising a set of switches configured to: when the stimulation generation circuitry provides the electrical stimulation, block the sensing signal from being received at an input of the first stage amplifier; and when the stimulation generation circuitry does not provide the electrical stimulation, allow the first amplified sensing signal to be received at the input of the first stage amplifier.

Example 5: The system of example 4, wherein, to block the sensing signal from being received at the input of the first stage amplifier, the set of switches is configured to block the sensing signal after a first time delay from when the stimulation generation circuitry no longer provides the electrical stimulation; and wherein, to block the first amplified sensing signal from being received at the input of the second stage amplifier, the set of blanking switches is configured to block the sensing signal after a second time delay from when the stimulation generation circuitry no longer provides the electrical stimulation, wherein the second time delay is different from the first time delay.

Example 6: The system of example 5, wherein the second time delay is longer than the first time delay.

Example 7: The system of example 3, further comprising a set of blanking switches configured to clamp a voltage of the sensing signal to a threshold voltage range.

Example 8: The system of example 7, wherein the threshold voltage range comprises a component safe voltage range.

Example 9: The system of any of examples 2-8, wherein the first stage amplifier comprises a transconductance amplifier.

Example 10: The system of any of examples 2-9, wherein the second amplifier stage is configured to auto-zero at input and comprises a direct transconductance amplifier.

Example 11: The system of example 10, wherein the amplifier circuitry comprises a third amplifier stage configured to receive an output of the second amplifier stage and to auto-zero at input, wherein the third amplifier stage comprises a linearized transconductance amplifier.

Example 12: The system of example 11, wherein the amplifier circuitry comprises a fourth amplifier stage configured to receive an output of the third amplifier stage and to auto-zero at input.

Example 13: The system of any of examples 9-12, wherein the processing circuitry is further configured to: when the stimulation generation circuitry provides the electrical stimulation, block the first amplified sensing signal from being received at an input of the second stage amplifier; and when the stimulation generation circuitry does not provide the electrical stimulation, allow the first amplified sensing signal to be received at the input of the second stage amplifier.

Example 14: The system of any of examples 2-13, further comprising injection circuitry configured to inject a cancelling offset between the first stage amplifier and the second stage of amplifier.

Example 15: The system of example 14, wherein the injection circuitry is further configured to generate the cancelling offset based on a weighted set of digital historical offsets of waveforms.

Example 16: The system of example 15, wherein the processing circuitry is configured to determine the weighted set of digital historical offsets of waveforms based on one or more previous sensing signals that occur before the sensing signal.

Example 17: The system of any of examples 15-16, wherein the injection circuitry is further configured to generate the cancelling offset by applying an integral controller on the weighted set of digital historical offsets of waveforms.

Example 18: The system of any of examples 1-17, wherein the processing circuitry is configured to: generate a waveform based on the sensing signal; perform a derivative operation on the waveform; after performing the derivative operation, apply a peak minus trough operation to the waveform to determine an amplitude value; and cause the stimulation generation circuitry to deliver the therapy based on the amplitude value.

Example 19: The system of example 18, wherein, to perform the derivative operation, the processing circuitry is configured to supply one zero at 1 on the unit circle; and wherein, to perform the peak minus trough operation, the processing circuitry is configured to supply one zero at 1 on the unit circle.

Example 20: The system of examples 18-19, wherein, to generate the waveform, the processing circuitry is further configured to determine an averaged waveform from the sensing signal and at least one other sensing signal.

Example 21: The system of examples 20, wherein the waveform is an finite impulse response (FIR) filtered waveform and wherein the processing circuitry is further configured to: apply a FIR filter to the averaged waveform generate the FIR filtered waveform.

Example 22: The system of any of examples 18-21, wherein the amplitude value comprises an evoked compound action potential (ECAP) amplitude value.

Example 23: The system of any of examples 1-22, wherein the sensing signal comprises an evoked compound action potential (ECAP) signal.

Example 24: The system of any of examples 1-23, wherein the therapy comprises one or more of spinal cord stimulation (SCS), deep brain stimulation (DBS), peripheral nerve stimulation (PNS), peripheral nerve field stimulation (PNFS), cortical stimulation (CS), pelvic floor stimulation, or gastrointestinal stimulation.

Example 25: The system of any of examples 1-24, wherein the stimulation generation circuitry, sensing circuitry, memory, and processing circuitry are arranged in a medical device.

Example 26: The system of any of examples 1-25, wherein medical device comprises an implantable medical device.

Example 27: A method comprising: when stimulation generation circuitry does not provide the electrical stimulation, causing, by processing circuitry, storage of a first voltage at a first terminal of sensing circuitry at a first calibration capacitor and causing, by the processing circuitry, storage of a second voltage at a second terminal of the sensing circuitry at a second calibration capacitor; after causing the storage of the first voltage at the first calibration capacitor and causing the storage of the second voltage at the second calibration capacitor and when the stimulation generation circuitry provides the electrical stimulation, switching out, by the processing circuitry, a first calibration switch to prevent the first voltage stored at the first calibration capacitor from changing and switching out, by the processing circuitry, a second calibration switch to prevent the second voltage stored at the second calibration capacitor from changing; while the first calibration switch is switched out and the second calibration switch is switched out and when the stimulation generation circuitry does not provide the electrical stimulation, determining, by the processing circuitry, a sensing signal based on the first voltage at the first terminal offset by a first calibration voltage stored by the first capacitor and based on the second voltage at the second terminal offset by a second calibration voltage stored by the second capacitor; and causing, by the processing circuitry, the stimulation generation circuitry to deliver the therapy to the patient based on the sensing signal.

Example 28: A medical device comprising: stimulation generation circuitry configured to provide electrical stimulation to the patient; sensing circuitry configured to sense a first voltage at a first terminal and to sense a second voltage at a second terminal; and processing circuitry electrically connected to the sensing circuitry and the stimulation generation circuitry, the processing circuitry being configured to: when the stimulation generation circuitry does not provide the electrical stimulation, cause storage of the first voltage at the first terminal at a first calibration capacitor and cause storage of the second voltage at the second terminal at a second calibration capacitor; after the first voltage is stored at the first calibration capacitor and the second voltage is stored at the second calibration capacitor and when the stimulation generation circuitry provides the electrical stimulation, switch out a first calibration switch to prevent the first voltage stored at the first calibration capacitor from changing and switch out a second calibration switch to prevent the second voltage stored at the second calibration capacitor from changing; while the first calibration switch is switched out and the second calibration switch is switched out and when the stimulation generation circuitry does not provide the electrical stimulation, determine, with the sensing circuitry, a sensing signal based on the first voltage at the first terminal offset by a first calibration voltage stored by the first capacitor and based on second voltage at the second terminal offset by a second calibration voltage stored by the second capacitor; and cause the stimulation generation circuitry to deliver the therapy to the patient based on the sensing signal.

Example 29: The medical device of example 28, further comprising amplifier circuitry configured to: receive the sensing signal; amplify, using a first stage amplifier and at least a second stage amplifier, the sensing signal to generate an amplified sensing signal; and wherein the processing circuitry is configured to cause the stimulation generation circuitry to deliver the therapy based on the amplified sensing signal.

Example 30: The medical device of example 29, wherein to amplify, the first stage amplifier amplifies the sensing signal to a first amplified sensing signal for output to the second stage amplifier and wherein the amplifier circuitry further comprises a set of blanking switches configured to: when the stimulation generation circuitry provides the electrical stimulation, block the first amplified sensing signal from being received at an input of the second stage amplifier; and when the stimulation generation circuitry does not provide the electrical stimulation, allow the first amplified sensing signal to be received at the input of the second stage amplifier.

Example 31: The medical device of example 30, further comprising a set of switches configured to: when the stimulation generation circuitry provides the electrical stimulation, block the sensing signal from being received at an input of the first stage amplifier; and when the stimulation generation circuitry does not provide the electrical stimulation, allow the first amplified sensing signal to be received at the input of the first stage amplifier.

Example 32: The medical device of example 31, wherein, to block the sensing signal from being received at the input of the first stage amplifier, the set of switches is configured to block the sensing signal after a first time delay from when the stimulation generation circuitry no longer provides the electrical stimulation; and wherein, to block the first amplified sensing signal from being received at the input of the second stage amplifier, the set of blanking switches is configured to block the sensing signal after a second time delay from when the stimulation generation circuitry no longer provides the electrical stimulation, wherein the second time delay is different from the first time delay.

Example 33: The medical device of example 32, wherein the second time delay is longer than the first time delay.

Example 34: The medical device of example 30, further comprising a set of blanking switches configured to clamp a voltage of the sensing signal to a threshold voltage range.

Example 35: The medical device of example 34, wherein the threshold voltage range comprises a component safe voltage range.

Example 36: The medical device of any of examples 29-35, wherein the first stage amplifier comprises a transconductance amplifier.

Example 37: The medical device of any of examples 29-36, wherein the second amplifier stage is configured to auto-zero at input and comprises a direct transconductance amplifier.

Example 38: The medical device of example 37, wherein the amplifier circuitry comprises a third amplifier stage configured to receive an output of the second amplifier stage and to auto-zero at input, wherein the third amplifier stage comprises a linearized transconductance amplifier.

Example 39: The medical device of example 38, wherein the amplifier circuitry comprises a fourth amplifier stage configured to receive an output of the third amplifier stage and to auto-zero at input.

Example 40: The medical device of any of examples 36-39, wherein the processing circuitry is further configured to: when the stimulation generation circuitry provides the electrical stimulation, block the first amplified sensing signal from being received at an input of the second stage amplifier; and when the stimulation generation circuitry does not provide the electrical stimulation, allow the first amplified sensing signal to be received at the input of the second stage amplifier.

Example 41: The medical device of any of examples 29-40, further comprising injection circuitry configured to inject a cancelling offset between the first stage amplifier and the second stage of amplifier.

Example 42: The medical device of example 41, wherein the injection circuitry is further configured to generate the cancelling offset based on a weighted set of digital historical offsets of waveforms.

Example 43: The medical device of examples 42, wherein the processing circuitry is configured to determine the weighted set of digital historical offsets of waveforms based on one or more previous sensing signals that occur before the sensing signal.

Example 44: The medical device of any of examples 42-43, wherein the injection circuitry is further configured to generate the cancelling offset by applying an integral controller on the weighted set of digital historical offsets of waveforms.

Example 45: The medical device of any of examples 28-44, wherein the processing circuitry is configured to: generate a waveform based on the sensing signal; perform a derivative operation on the waveform; after performing the derivative operation, apply a peak minus trough operation to the waveform to determine an amplitude value; and cause the stimulation generation circuitry to deliver the therapy based on the amplitude value.

Example 46: The medical device of example 45, wherein, to perform the derivative operation, the processing circuitry is configured to supply one zero at 1 on the unit circle; and wherein, to perform the peak minus trough operation, the processing circuitry is configured to supply one zero at 1 on the unit circle.

Example 47: The medical device of examples 45-46, wherein, to generate the waveform, the processing circuitry is further configured to determine an averaged waveform from the sensing signal and at least one other sensing signal.

Example 48: The medical device of example 47, wherein the waveform is an finite impulse response (FIR) filtered waveform and wherein the processing circuitry is further configured to: apply a FIR filter to the averaged waveform generate the FIR filtered waveform.

Example 49: The medical device of any of examples 45-48, wherein the amplitude value comprises an evoked compound action potential (ECAP) amplitude value.

Example 50: The medical device of any of examples 28-49, wherein the sensing signal comprises an evoked compound action potential (ECAP) signal.

Example 51: The medical device of any of examples 28-50, wherein the therapy comprises one or more of spinal cord stimulation (SCS), deep brain stimulation (DBS), peripheral nerve stimulation (PNS), peripheral nerve field stimulation (PNFS), cortical stimulation (CS), pelvic floor stimulation, or gastrointestinal stimulation.

Example 52: The medical device of any of examples 28-51, wherein medical device comprises an implantable medical device.

Example 53: A system for providing therapy to a patient, the system comprising: stimulation generation circuitry configured to provide electrical stimulation to the patient; sensing circuitry configured to sense a sensing signal; and processing circuitry electrically connected to the sensing circuitry and stimulation generation circuitry; and amplifier circuitry configured to: receive the sensing signal from the sensing circuitry; amplify, using a transconductance amplifier, the sensing signal to generate a first amplified sensing signal; when the stimulation generation circuitry provides the electrical stimulation, block the first amplified sensing signal from being received at an input of a second stage amplifier; when the stimulation generation circuitry does not provide the electrical stimulation, allow the first amplified sensing signal to be received at the input of the second stage amplifier; amplify, using the second stage amplifier, the first amplified sensing signal, to generate a second amplified signal; and wherein the processing circuitry is configured to cause the stimulation to deliver the therapy based on the second amplified sensing signal.

Example 54: The system of example 53, wherein the amplifier circuitry further comprises a set of blanking switches configured to: when the stimulation generation circuitry provides the electrical stimulation, block the first amplified sensing signal from being received at an input of the second stage amplifier; and when the stimulation generation circuitry does not provide the electrical stimulation, allow the first amplified sensing signal to be received at the input of the second stage amplifier.

Example 55: The system of example 54, further comprising a set of switches configured to: when the stimulation generation circuitry provides the electrical stimulation, block the sensing signal from being received at an input of the first stage amplifier; and when the stimulation generation circuitry does not provide the electrical stimulation, allow the first amplified sensing signal to be received at the input of the first stage amplifier.

Example 56: The system of example 55, wherein, to block the sensing signal from being received at the input of the first stage amplifier, the set of switches is configured to block the sensing signal after a first time delay from when the stimulation generation circuitry no longer provides the electrical stimulation; and wherein, to block the first amplified sensing signal from being received at the input of the second stage amplifier, the set of blanking switches is configured to block the sensing signal after a second time delay from when the stimulation generation circuitry no longer provides the electrical stimulation, wherein the second time delay is different from the first time delay.

Example 57: The system of example 56, wherein the second time delay is longer than the first time delay.

Example 58: The system of example 53, further comprising a set of blanking switches configured to clamp a voltage of the sensing signal to a threshold voltage range.

Example 59: The system of example 58, wherein the threshold voltage range comprises a component safe voltage range.

Example 60: A system for providing therapy to a patient, the system comprising: stimulation generation circuitry configured to provide electrical stimulation to the patient; sensing circuitry configured to sense a sensing signal; and processing circuitry electrically connected to the sensing circuitry and stimulation generation circuitry, the processing circuitry being configured to: receive the sensing signal from the sensing circuitry; amplify, using a transconductance amplifier, the sensing signal to generate a first amplified sensing signal; when the stimulation generation circuitry provides the electrical stimulation, block the first amplified sensing signal from being received at an input of a second stage amplifier; when the stimulation generation circuitry does not provide the electrical stimulation, allow the first amplified sensing signal to be received at the input of the second stage amplifier; amplify, using the second stage amplifier, the first amplified sensing signal, to generate a second amplified signal; and wherein the processing circuitry is configured to cause the stimulation generation therapy to deliver the therapy based on the second amplified sensing signal.

Example 61: The system of example 60, wherein the second amplifier stage is configured to auto-zero at input and comprises a direct transconductance amplifier.

Example 62: The system of example 61, wherein the amplifier circuitry comprises a third amplifier stage configured to receive an output of the second amplifier stage and to auto-zero at input, wherein the third amplifier stage comprises a linearized transconductance amplifier.

Example 63: The system of example 62, wherein the amplifier circuitry comprises a fourth amplifier stage configured to receive an output of the third amplifier stage and to auto-zero at input.

Example 64: The system of any of examples 60-63, wherein the processing circuitry is further configured to: when the stimulation generation circuitry provides the electrical stimulation, block the first amplified sensing signal from being received at an input of the second stage amplifier; and when the stimulation generation circuitry does not provide the electrical stimulation, allow the first amplified sensing signal to be received at the input of the second stage amplifier.

Example 65: A method comprising performing the operation of any of examples 1-64.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), such as, for example, ferroelectric RAM (FRAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A system for providing therapy to a patient, the system comprising:

stimulation generation circuitry configured to provide electrical stimulation to the patient;

sensing circuitry configured to sense a first voltage at a first terminal and to sense a second voltage at a second terminal; and processing circuitry electrically connected to the sensing circuitry and the stimulation generation circuitry, the processing circuitry being configured to:

in a first time, when the stimulation generation circuitry does not provide the electrical stimulation, cause storage of the first voltage at the first terminal at a first calibration capacitor and storage of the second voltage at the second terminal at a second calibration capacitor, wherein, in the first time, the first voltage stored at the first calibration capacitor is a first calibration voltage and the second voltage stored at the second calibration capacitor is a second calibration voltage;

in a second time, after the first calibration capacitor stores the first calibration voltage in the first time and the second calibration capacitor stores the second calibration voltage in the first time and when the stimulation generation circuitry provides the electrical stimulation, switch out a first calibration switch to prevent the first calibration voltage stored at the first calibration capacitor from changing and switch out a second calibration switch to prevent the second calibration voltage stored at the second calibration capacitor from changing;

in a third time after the second time, while the first calibration switch is switched out and the second calibration switch is switched out and when the stimulation generation circuitry does not provide the electrical stimulation, determine, with the sensing circuitry, a sensing signal based on a first signal acquisition voltage offset by a first offset voltage and based on a second signal acquisition voltage offset by a second offset voltage, wherein the first offset voltage is based on the first calibration voltage, and wherein the second offset voltage is based on the second calibration voltage; and cause the stimulation generation circuitry to deliver the therapy to the patient based on the sensing signal.

2. The system of claim 1, further comprising amplifier circuitry configured to:

receive the sensing signal;

amplify, using a first stage amplifier and at least a second stage amplifier, the sensing signal to generate an amplified sensing signal; and wherein the processing circuitry is configured to cause the stimulation generation circuitry to deliver the therapy based on the amplified sensing signal.

3. The system of claim 2, wherein to amplify, the first stage amplifier amplifies the sensing signal to a first amplified sensing signal for output to the second stage amplifier and wherein the amplifier circuitry further comprises a set of blanking switches configured to:

when the stimulation generation circuitry provides the electrical stimulation, block the first amplified sensing signal from being received at an input of the second stage amplifier; and when the stimulation generation circuitry does not provide the electrical stimulation, allow the first amplified sensing signal to be received at the input of the second stage amplifier.

4. The system of claim 3, further comprising a set of switches configured to:

when the stimulation generation circuitry provides the electrical stimulation, block the sensing signal from being received at an input of the first stage amplifier; and when the stimulation generation circuitry does not provide the electrical stimulation, allow the first amplified sensing signal to be received at the input of the first stage amplifier.

5. The system of claim 4, wherein, to block the sensing signal from being received at the input of the first stage amplifier, the set of switches is configured to block the sensing signal after a first time delay from when the stimulation generation circuitry no longer provides the electrical stimulation; and wherein, to block the first amplified sensing signal from being received at the input of the second stage amplifier, the set of blanking switches is configured to block the sensing signal after a second time delay from when the stimulation generation circuitry no longer provides the electrical stimulation, wherein the second time delay is different from the first time delay.

6. The system of claim 5, wherein the second time delay is longer than the first time delay.

7. The system of claim 3, further comprising a set of blanking switches configured to clamp a voltage of the sensing signal to a threshold voltage range.

8. The system of claim 7, wherein the threshold voltage range comprises a component safe voltage range.

9. The system of claim 2, wherein the first stage amplifier comprises a transconductance amplifier.

10. The system of claim 2, wherein the second amplifier stage is configured to auto-zero at input and comprises a direct transconductance amplifier.

11. The system of claim 10, wherein the amplifier circuitry comprises a third amplifier stage configured to receive an output of the second amplifier stage and to auto-zero at input, wherein the third amplifier stage comprises a linearized transconductance amplifier.

12. The system of claim 11, wherein the amplifier circuitry comprises a fourth amplifier stage configured to receive an output of the third amplifier stage and to auto-zero at input.

13. The system of claim 9, wherein the processing circuitry is further configured to:

when the stimulation generation circuitry provides the electrical stimulation, block the first amplified sensing signal from being received at an input of the second stage amplifier; and when the stimulation generation circuitry does not provide the electrical stimulation, allow the first amplified sensing signal to be received at the input of the second stage amplifier.

14. The system of claim 2, further comprising injection circuitry configured to inject a cancelling offset between the first stage amplifier and the second stage of amplifier.

15. The system of claim 14, wherein the injection circuitry is further configured to generate the cancelling offset based on a weighted set of digital historical offsets of waveforms.

16. The system of claim 15, wherein the processing circuitry is configured to determine the weighted set of digital historical offsets of waveforms based on one or more previous sensing signals that occur before the sensing signal.

17. The system of claim 15, wherein the injection circuitry is further configured to generate the cancelling offset by applying an integral controller on the weighted set of digital historical offsets of waveforms.

18. The system of claim 1, wherein the processing circuitry is configured to:

generate a waveform based on the sensing signal;

perform a derivative operation on the waveform;

after performing the derivative operation, apply a peak minus trough operation to the waveform to determine an amplitude value; and cause the stimulation generation circuitry to deliver the therapy based on the amplitude value.

19. A method comprising:

in a first time, when stimulation generation circuitry does not provide electrical stimulation, causing, by processing circuitry, storage of a first voltage at a first terminal of sensing circuitry at a first calibration capacitor and causing, by the processing circuitry, storage of a second voltage at a second terminal of the sensing circuitry at a second calibration capacitor, wherein, in the first time, the first voltage stored at the first calibration capacitor is a first calibration voltage and the second voltage stored at the second calibration capacitor is a second calibration voltage;

in a second time, after the first calibration capacitor stores the first calibration voltage in the first time and the second calibration capacitor stores the second calibration voltage in the first time and when the stimulation generation circuitry provides the electrical stimulation, switching out, by the processing circuitry, a first calibration switch to prevent the first calibration voltage stored at the first calibration capacitor from changing and switching out, by the processing circuitry, a second calibration switch to prevent the second calibration voltage stored at the second calibration capacitor from changing;

in a third time after the second time, while the first calibration switch is switched out and the second calibration switch is switched out and when the stimulation generation circuitry does not provide the electrical stimulation, determining, by the processing circuitry, a sensing signal based on a first signal acquisition voltage offset by a first offset voltage and based on a second signal acquisition voltage offset by a second offset voltage, wherein the first offset voltage is based on the first calibration voltage, and wherein the second offset voltage is based on the second calibration voltage; and causing, by the processing circuitry, the stimulation generation circuitry to deliver therapy to a patient based on the sensing signal.

20. A medical device comprising:

stimulation generation circuitry configured to provide electrical stimulation to a patient;

sensing circuitry configured to sense a first voltage at a first terminal and to sense a second voltage at a second terminal; and processing circuitry electrically connected to the sensing circuitry and the stimulation generation circuitry, the processing circuitry being configured to:

in a first time, when the stimulation generation circuitry does not provide the electrical stimulation, cause storage of the first voltage at the first terminal at a first calibration capacitor and cause storage of the second voltage at the second terminal at a second calibration capacitor, wherein, in the first time, the first voltage stored at the first calibration capacitor is a first calibration voltage and the second voltage stored at the second calibration capacitor is a second calibration voltage;

in a second time, after the first calibration capacitor stores the first calibration voltage in the first time and the second calibration capacitor stores the second calibration voltage in the first time and when the stimulation generation circuitry provides the electrical stimulation, switch out a first calibration switch to prevent the first calibration voltage stored at the first calibration capacitor from changing and switch out a second calibration switch to prevent the second calibration voltage stored at the second calibration capacitor from changing;

in a third time after the second time, while the first calibration switch is switched out and the second calibration switch is switched out and when the stimulation generation circuitry does not provide the electrical stimulation, determine, with the sensing circuitry, a sensing signal based on a first signal acquisition voltage offset by a first offset voltage and based on a second signal acquisition voltage offset by a second offset voltage, wherein the first offset voltage is based on the first calibration voltage, and wherein the second offset voltage is based on the second calibration voltage; and cause the stimulation generation circuitry to deliver therapy to the patient based on the sensing signal.

* * * * *